United States Patent
Leigh et al.

(10) Patent No.: US 6,599,527 B1
(45) Date of Patent: *Jul. 29, 2003

(54) PREPARATION OF PHARMACEUTICAL COMPOSITIONS

(75) Inventors: Steven Leigh, Warlingham (GB); Mathew Louis Steven Leigh, Warlingham (GB)

(73) Assignee: Phares Pharmaceutical Research N.V., Curacao (AN)

(*) Notice: Subject to any disclaimer, the term of this patent is extended or adjusted under 35 U.S.C. 154(b) by 0 days.

This patent is subject to a terminal disclaimer.

(21) Appl. No.: 09/466,265

(22) Filed: Dec. 17, 1999

Related U.S. Application Data

(63) Continuation of application No. PCT/GB98/01803, filed on Jun. 19, 1998.

(30) Foreign Application Priority Data

Jun. 20, 1997 (GB) .................................. 9713140

(51) Int. Cl.⁷ .............................. A61K 9/48; A61K 9/20; A61K 9/00
(52) U.S. Cl. ........................ 424/451; 424/400; 424/464; 424/489; 514/9; 514/763
(58) Field of Search ................... 424/400, 451, 424/464, 489, 1.21, 9.321, 9.51, 417, 450; 514/9, 763

(56) References Cited

U.S. PATENT DOCUMENTS

| 4,158,707 A | | 6/1979 | Steffen et al. ............... 424/244 |
| 4,298,594 A | | 11/1981 | Sears et al. .................... 424/19 |
| 4,830,858 A | * | 5/1989 | Payne ......................... 424/450 |
| 5,009,956 A | * | 4/1991 | Baumann ................. 428/402.2 |
| 5,043,164 A | * | 8/1991 | Huang ......................... 424/423 |
| 5,053,217 A | * | 10/1991 | Leigh ............................ 424/45 |
| 5,141,674 A | * | 8/1992 | Leigh ......................... 252/305 |
| 5,178,875 A | * | 1/1993 | Lenk ........................... 424/450 |
| 5,221,696 A | * | 6/1993 | Ke ............................... 514/786 |
| 5,529,785 A | | 6/1996 | Dietl ........................... 424/450 |
| 5,756,450 A | | 5/1998 | Hahn et al. ..................... 514/9 |

FOREIGN PATENT DOCUMENTS

| AU | 24805/84 | 8/1984 | ......... A61K/47/00 |
| AU | 16202/97 | 9/1997 | ......... A23L/1/275 |
| DE | 4003782 | * 8/1991 | |
| EP | 0158441 | 10/1985 | ............ A61K/9/50 |
| EP | 0282405 | 9/1988 | ............ A61K/9/50 |

(List continued on next page.)

OTHER PUBLICATIONS

"Concise Chemical And Technical Dictionary, 1986, Chemical Publishing Company, Inc., ISBN 0–8206–0310–4", p. 791.

Standard encyclopedia of chemistry Fachlexikon ABC Chemie, Band 1 A–K, 1979, Verlag Harri Deutsch, Thun, Frankfurt, ISBN 3 87144 0027, p. 306.

Fahr, A., et al., "Liposomal Formulations of Cyclosporin A: Influence of Lipid Type and Dose on Pharmacokinetics", *Pharmaceutical Research*, 12 (8), pp. 1189–1198, (Aug. 1995).

(List continued on next page.)

Primary Examiner—Gollamudi S. Kishore
(74) Attorney, Agent, or Firm—Burns, Doane, Swecker and Mathis, LLP

(57) ABSTRACT

A substantially homogeneous composition for human administration comprises a biologically active lipophilic compound dissolved in or associated with at least one micelle-forming lipid. For example, cyclosporin A is dissolved or dispersed in the mixture of PC and MAPC. The composition may be made by dissolving the lipid material in ethanol, adding the lipophilic compound to the ethanol and removing the ethanol, after which the composition may be formulated for human oral administration.

46 Claims, 12 Drawing Sheets

FOREIGN PATENT DOCUMENTS

| | | | |
|---|---|---|---|
| EP | 0355095 | 2/1990 | ............ A61K/9/42 |
| EP | 0429248 | 5/1991 | .......... A61K/9/107 |
| EP | 0697214 | 2/1996 | .......... A61K/9/127 |
| EP | 0700678 | 3/1996 | .......... A61K/9/107 |
| EP | 0712631 | 5/1996 | .......... A61K/38/13 |
| EP | 0760237 | 3/1997 | .......... A61K/9/107 |
| GB | 0505983 | 5/1939 | |
| GB | 2018712 | 10/1979 | ............ A61K/9/50 |
| GB | 2257359 | 1/1993 | .......... A61K/37/02 |
| JP | 622 79832 | * 12/1987 | |
| WO | 88/06438 | 9/1988 | ............ A61K/9/42 |
| WO | 88/07362 | 10/1988 | ............ A61K/7/06 |
| WO | 94/26254 | * 11/1994 | |
| WO | 98/33512 | 8/1998 | .......... A61K/38/13 |
| WO | 98/58629 | 12/1998 | .......... A61K/9/107 |

OTHER PUBLICATIONS

Guzman, M., et al., "Formation and Characterization of Cyclosporine–Loaded Nanoparticles", *Journal of Pharmaceutical Sciences*, 82 (5), pp. 498–502, (May 1993).

Kavorik, J.M., et al., "Reduced Inter– and Intraindividual Variability in Cyclosporine Pharmacokinetics from a Microemulsion Formulation", *Journal of Pharmaceutical Sciences*, 83 (3), pp. 444–446, (Mar. 1994).

Sato, H., et al., "Enhancement of the Intestinal Absorption of a Cyclosporine Derivative by Milk Fat Globule Membrane", *Biological & Pharmaceutical Bulletin*, 17 (11), pp. 1526–1528, (1994).

Sokol, R.J., et al., "Improvement of cyclosporin absorption in children after liver transplantation by means of water–soluble vitamin E", *The Lancet*, 338 (8761), pp. 212–215, (Jul. 27, 1991).

Vudathala, G.K., et al., "Dissolution of Fludrocortisone from Phospholipid Coprecipitates", *Journal of Pharmaceutical Sciences*, 81 (3), pp. 282–286, (Mar. 1992).

Yonish–Rouach, E., et al., "A method for preparing biologically active aqueous cyclosporin A solutions avoiding the use of detergents or organic solvents", *Journal of Immunological Methods*, 135 (1–2), pp. 147–153, (1990).

* cited by examiner

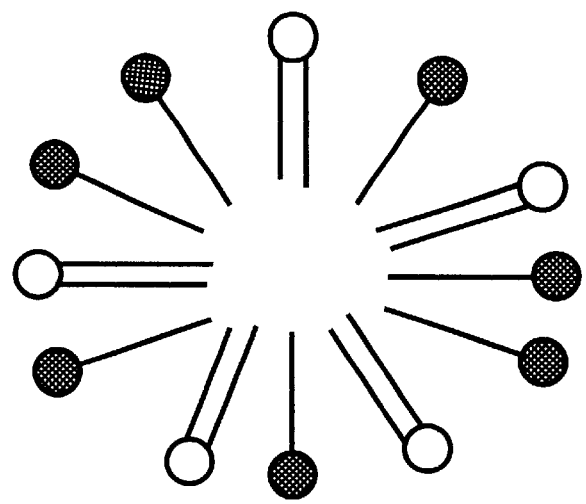
FIG. 1C
FIG. 2
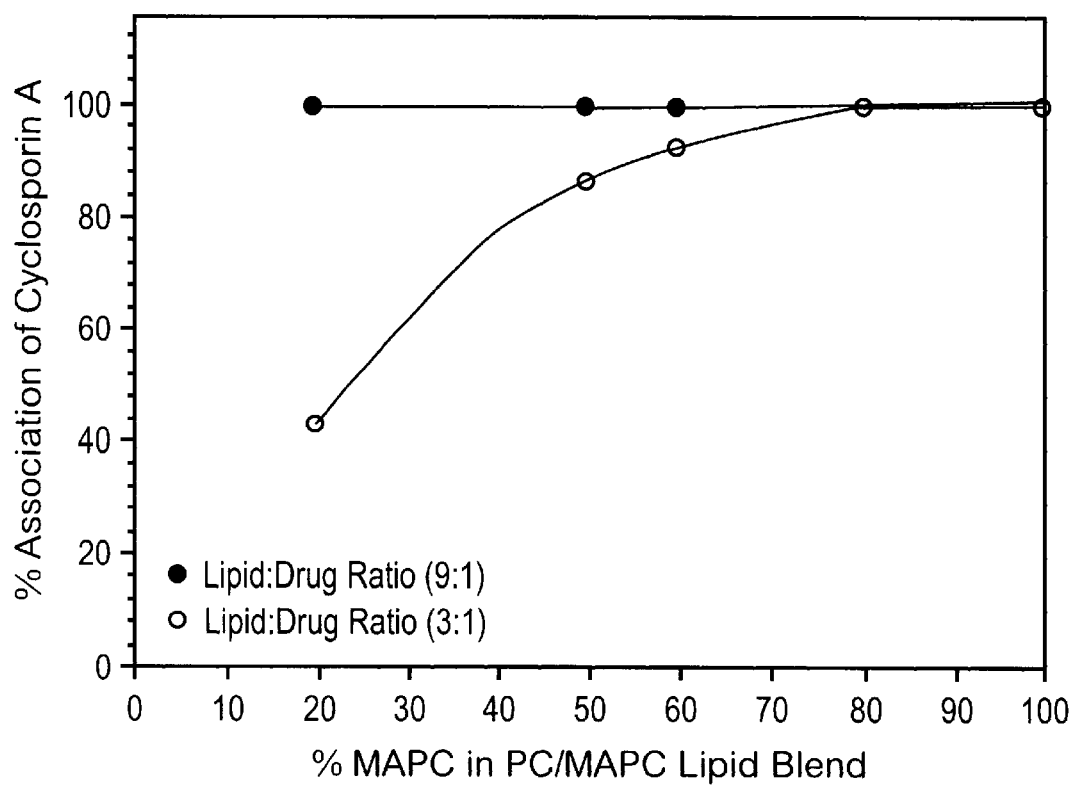

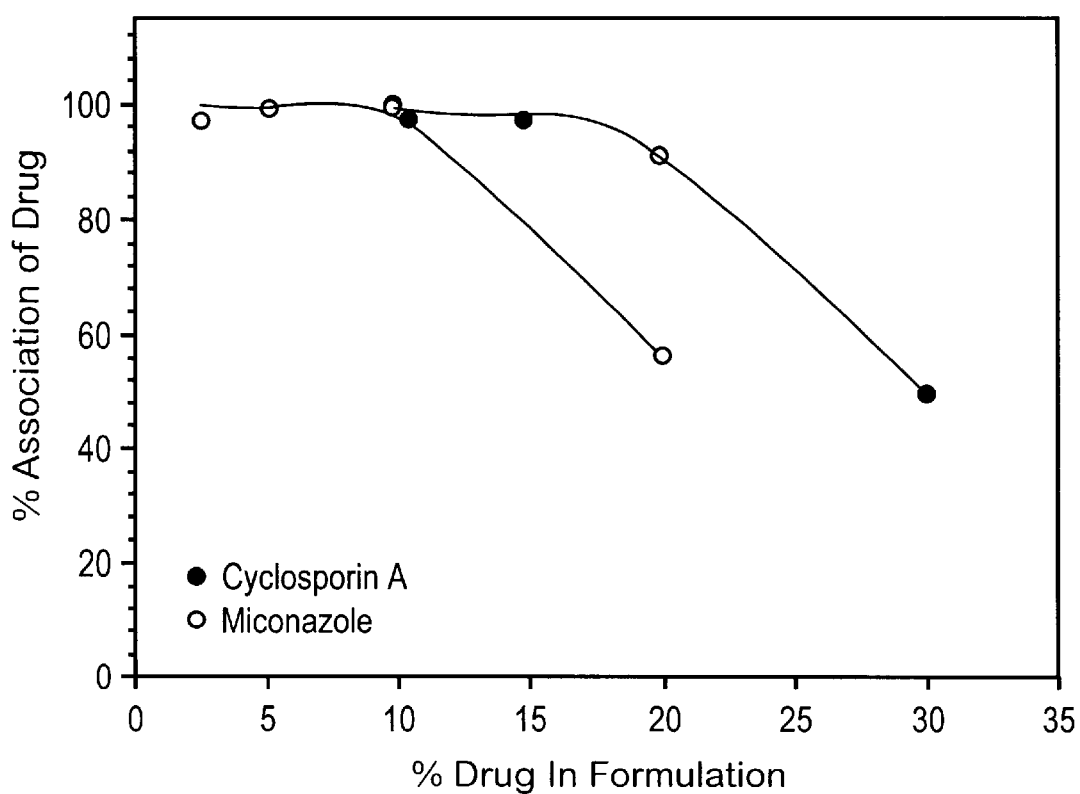

PREPARATION OF PHARMACEUTICAL COMPOSITIONS

CROSS-REFERENCE TO RELATED APPLICATIONS

This application is a continuation of International Patent Application No. PCT/GB98/01803, filed on Jun. 19, 1998, which in turn is an international filing of British Patent Application No. 9713140.3, filed on Jun. 20, 1997, both of which are incorporated herein by reference.

FIELD OF THE INVENTION

The present invention relates to the preparation of carriers for lipophilic materials in general. More specifically it relates to the formation of an improved carrier for these compounds which disperses in the presence of the aqueous contents of the gastro-intestinal tract (GI) to form drug-carrying lipid aggregates. The invention is particularly suitable for oral applications but can be readily adapted for other uses. The invention especially relates to novel phospholipid-cyclosporin formulations having improved bio-availability, increased efficacy and reduced toxicity and to a process of manufacture of such formulations.

BACKGROUND TO THE INVENTION

Cyclosporins are fungal metabolites. They are hydrophobic neutral cyclic peptides and have essentially similar chemical and physical properties. Cyclosporin A (CyA) is representative and is the best known example. It is widely used in organ transplants to prevent rejection and as an immunosupressive agent in the treatment of systemic and local autoimmune disorders in which T cells play a major role. CyA has also been used to treat chronic conditions such as rheumatoid arthritis, asthma and non-malignant skin disorders. Derivatives of CyA are also known to prevent multi-drug resistance from developing during treatment with cytotoxic drugs.

The clinical use of CyA in oral and intravenous dosage forms to prevent organ rejection was approved by the FDA in 1983. It has dramatically improved long-term survival rates in transplant patients. Most patients, however, still need to be maintained on life-long CyA therapy. This is normally provided in an oral form but may involve intravenous injection when it is necessary to obtain an adequate blood concentration quickly or oral therapy proves ineffective. Unfortunately, there are two major problems associated with oral therapy. Firstly, since the drug is lipophilic, its absorption from the GI tract is variable and incomplete, and bioavailability can range from 6% to 60%. This results in variable or inadequate blood concentrations which can bring about graft rejection and failure Secondly, use of CyA is associated with nephrotoxicity. Impairment in kidney function is dose-related and increases with prolonged exposure, again emphasising the importance of controllable and predictable bioavailability.

There are few therapeutic compounds that have received more extensive and exhaustive pharmacodynamic and pharmacokinetic examination than CyA. Investigations have shown that CyA has a narrow therapeutic index and that drug absorption takes place across an absorption window located along the upper part of the small intestine. Little absorption takes place in the stomach or colon.

The first CyA oral formulation introduced into clinical use (Sandimmune) comprised a solution of CyA dissolved in a solvent system of olive oil and ethanol (Patentschrift (Switz.) CH 64I 356, Feb. 29, 1984, Appl. 79/1949. Feb. 27, 1979). The oil was emulsified in water using a polyethoxylated oleic glyceride surfactant to give a coarse O/W emulsion. This system was found to be inherently thermodynamically unstable. It is markedly affected by external conditions such as pH, temperature, diluting medium surrounding medium As a result, drug tended to precipitate out of solution, and thus not be absorbed. The release of CyA from the oil-droplets and its subsequent absorption was also found to be highly dependent on the prevailing conditions in the GI tract e.g. composition of food and presence of bile and pancreatic enzymes. This formulation thus gave erratic inter- and intra-patient bioavailability.

Although these problems were widely recognised, Sandimmune was relied upon exclusively by transplant patients for a number of years. It is only recently that a new oral formulation of CyA called Neoral with improved pharmacokinetics has been introduced to address these problems. This formulation was introduced as a 'high-technology' microemulsion system in which the CyA is dissolved in a solvent consisting of a mixed lipophilic (corn oil mono-, di- and triglycerides) and hydrophilic (propylene glycol) solvent stabilised by an appropriate amount of a powerful surfactant, polyoxyl-40 hydrogenated castor oil (Kovarik et al, J. Pharm Sciences, 83, 444 (1994), and Hall, Inpharm, 10 December p 13 (1994)). This new formulation is reported to have self-emulsifying properties and immediately forms a transparent microemulsion in aqueous fluids. The CyA is dissolved in colloidal oil droplets (10–100 nm diameter) stabilised by the surfactant and can be diluted without precipitation, having similar properties to a real aqueous solution.

Neoral is at present the only known oral formulation generally available that gives consistent absorption, independent of bile and food. Clearly, in view of the number of patients world-wide who need to be on long-term CyA maintainance and their individual circumstances, it would be most desirable for there to be a comparable bioequivalent formulation that does not rely on the presence of potentially harmful synthetic surfactants.

A number of alternative approaches to the solubilisation of CyA and the development of formulations that avoid the dual problems of variable bioavailabilty and incomplete absorption from the GI tract have been described in the prior art.

Polyvinyl pyrollidone (PVP) with molecular weights of 40,000 and 17,000, have been used as solubilising agent to carry the drug (Yonish-Rouach et al Journal of Immunological Methods 135, 147–153 (1990)). It was demonstrated that CyA can be solubillsed and retain its activity (in vitro) in aqueous solutions of PVP. However, no evidence that the formulation would work in vivo was presented.

Co-administration of d-alphatocopheryl polyethylene glycol succinate (TPGS) which can form micelles has been reported to lead to an improvement of CyA absorption in children after liver transplantation (Sokol et al., The Lancet 338, 212–215, (1991)).

In order to counter the poor solubility of CyA, Guzman et al., have immobdilsed the drug in nanoparticles of polymeric nanomatrix composed of either isobutyl-2-cyanoacrylate monomer or poly-E-caprolactone, in the presence of Pluronic F-68 (Journal of Pharmaceutical Sciences 82, 498–502 (1993)). However, the drug-free nanoparticles also exhibited immunosupressive activity suggesting that they are unlikely to be a suitable vector for carrying CyA.

The enhancement of the intestinal absorption of a cyclosporine derivative (used as a model for CyA) by using milk fat globule membrane (MFGM) as an emulsifier of lipophilic cyclopeptides has been reported (Biol. Pharm. Bull. 17, 1526–1528(1994)).

In cases, where it is necessary to administer CyA intraveneously, it is normally formulated in an injectable form using a solvent consisting of ethanol and Cremophor EL, a tri-ricinoleate ester of ethoxylated castor oil. This solubiliser frequently gives rise to anaphylatic reactions and is itself known to cause nephrotoxicity exacerbating problems associated with the inherent renal toxicity of CyA.

A well-recognised approach to the formulation of lipophilic drugs is liposome encapsulation in which the drug is intercalated into the lipid bilayer(s) of the liposome. Compositions, methods of preparation, applications, advantages and disadvantages of liposomes have all been extensively reported, and there are more than 30 publications describing liposomal entrapment of CyA mainly for intravenous and systemic use.

From purely pharmaceutical considerations, there is general consensus that liposome entrapment significantly reduces nephrotoxicity. However, there is less certainty about whether the reduced nephrotoxicity reported with intravenous liposomal formulations is in fact due to altered pharmacokinetics of liposome encapsulated CyA or the non-specific, physical binding of the drug to other lipids present in the system. Some reports claim that CyA pharmacolknetics depend on such factors as liposome charge, size and composition. Fahr (Pharmaceutical Research, 12, 1189–1198 (1995)), however, dismisses this idea and cites evidence suggesting that high lipid doses tend to bind CyA in blood, thereby minimising the amount of drug available in sensitive organs like the kidney.

Apart from factors influencing the inherent nephrotoxicity of CyA, the three key factors in determining the suitability of carriers for CyA for oral and systemic use are: that the vector system should be non-toxicirrirritant, it should have high entrapment levels and it should be stable.

Membrane lipids are present in all living cells and represent a significant component of our diet and thus their use present no toxicity problems. There are, however. problems regarding entrapment levels and stability, The charge, nature of the headgroups, and the saturation of the hydrocarbon chains have all been shown to influence the level of entrapment of CyA in liposomes. There is, however, consensus amongst those engaged in lposome work that the lipid:CyA molar ratio at equilibrium is about 20:1 for egg phosphatidylcholine. This should, however, be considered as a lower limit as in our own experience, unless the lipid:drug ratio is substantially greater than 20:1, the bound CyA in the liposome membrane will diffuse out into the surrounding aqueous medium and will precipitate out as untrapped CyA crystals on standing.

This problem is not fully recognised and many of the earlier studies, particularly those in which drug entrapment is measured by the analysis of liposomal pellets obtained by ultracentrifugation and no account is taken of the proportion of non-entrapped drug, tend to cite unrealistically high entrapment values. This is of importance as it is well known in formulation work that free CyA crystals are not absorbed from the GI tract resulting in poor bioavailability. In the case of intravenous injection, the formation of CyA crystals must be avoided at all costs. In practice, it is this crystallisation process that is the main reason why many liposome formulations perform so badly and do not proceed beyond animal testing.

EP 0 697 214 A1, describes aqueous compositions, with liposomes having a siz less than 100 nm, prepared by homogenising a specific mixture of a phosphatidylcholine, phosphatidyl glycerol and cyclosporin in a mole ratio of from 25:3:1 to 17:3:1. The claims for particle size and drug entrapment would appear to render the compositions suitable for intravenous administration of CyA.

PCT Publication No: 90/00389 discloses a method for the preparation of freeze-dried compositions of CyA in liposomes. The liposomes are intended to be reconstituted immediately before use in an attempt to solve the problems of stability and crystal formation. It discloses lipid:drug ratios in the region of 20:1.

EP 0 355 095 describes a pharmacological agent-lipid solution preparation comprising a lipophilic pharmacological agent, which may be CyA, a desalted charged lipid and an aqueous-miscible lipid solvent such that uponr introduction into an aqueous medium a suspension of lipid associated with the pharmacological agent is formed. As such it is clearly an example of the prior art pro-liposome compositions containing charged lipids, disclosed in the earlier EP 0 158 441.

Even if the formulations described in both the above disclosures have successfully managed to overcome these problems, they would still be exceedingly expensive to produce because of the lipids used, particularly at the high lipid/drug ratios involved, and the relatively complex production processes involved.

In general, technical problems relating to entrapment and stability combined with high production costs have, to date, limited the wider use of liposomes as carriers for drugs. Only amphotericin and doxorubicin are presently in clinical use. These products are for lifethreatening conditions and the quantities used are relatively small to justify the high costs of the lpids and the complex manufacturing processes involved.

Apart from their use in liposomes, there is some report in the prior art describing the use of phospholipids for improving the dissolution of oil-soluble compounds or improving their absorption from the GI tract.

The preparation of solid lipid-drug co-precipitates using diacyl phospholipids to increase the dissolution behaviour of poorly water-soluble drug solvates, and the possibility of modifying drug release from such dispersions by incorporation of small amounts of polymers, has been described (J. Pharm. Sci. 81, 282–286 (1992)). The amount of phospholipid employed, was much lower than the amount of drug and these preparations involved the incorporation of lipid in the crystalline structure of the drug solvate.

PCT/US86/00637 discloses the use of non-esterified fatty acids and monoglycerides in molar ratios between 1:2 and 2:1 together with up to 30 mole percent of a monacyl lipid, lyso-phosphatidylchouine, to form lipid particles which show improved oral absorption when used as carriers for various lipophilic compounds.

Vehicles described as circulating micro-reservoirs, suitable for delivering xenobiotics are disclosed in U.S. Pat. No. 4,298,594. The compositions consist of diacyl phospholipids together with sufficient cholesterol esters to render them more hydrophobic. They are claimed to give improved in vitro and in vivo stability to lipophilic drugs as well as enhanced oral absorption.

U.S. Pat. No. 5,009,956 discloses a method of stabilising small unilamellar vesicles (SUVs) having an outer and an inner layer, comprising between 15–32.5 mol percent of a monoacyl phospholipid in the outer layer of the singlebilayer membrane. It is claimed that sonication of a mixture of diacyl and monoacyl lipids in the proportions stated, for a period of time, is necessary in order to equilibrate the mixture of lipids and obtain maximal stabilisation. There is no suggestion that the SUVs described can be used to solubilise large amounts of lipophilic compounds through molecular association.

SUMMARY OF THE INVENTION

An object of the present invention is to provide a bulk lipid carrier, particularly for lipophilic compounds, that is safe, efficient and effective. The existing carriers for lipophilic compounds are systems based on combinations of hydrophilic and lipophilic solvents and ethoxylated chemical surfactants. Although the carrying capacity may be adequate, some compositions can be potentially harmful, particularly if administered in large amounts over a prolonged period.

Given the many benefits of phospholipids, it would be highly desirable to find a means to exploit their unique carrier potential without the practical limitations of presently available systems. The work reported in the prior art points to the need for an efficient, effective and non-toxic carrier for lipophilic compounds. Such needs are not unique to the cyclosporins. There are many biologically active compounds where optimum bioavailibilty cannot be expressed because of poor solubility. For example, in some of the new antifungal and cytotoxic compounds, activity is often linked with lipophilicity. Many lipophilic drug candidates do not progress to further clinical evaluation because of the inability to formulate a suitable dosage form that would allow the potential benefits of the compound to be assessed. Therefore, a non-toxic carrier that transports lipophilic compounds in molecular dispersion would be of significant benefit.

In one aspect, the present invention employs the solubilisation of lipophilic drugs such as CyA in mixtures of diacyl lipids, for example pliosphatidyl choline (PC) and monoacyl lipids, for example mono-acyl phosphatidyl choline (MAPC).

The reasons for the use of such mixtures is three-fold. Firstly, we find that such mixtures are capable of solubilising much higher amounts of CyA than diacyl lipids alone. The reasons for this are not clear but may reflect an association due to steric factors and/or membrane topography. Secondly, the presence of the monoacyl lipid appears to enhance the dispesability of these mixtures in aqueous media. Thirdly, the bioavailability of CyA (or other lipophilic compound) is greatly improved. The reasons for this are again not fully dear but are probably related to the fact that PC and fat-soluble compounds such as CyA are absorbed in the same region of the gastro-intestinal tract.

The absorption, transport and phanmacokinetics of phospholipids are well-known. Over 90% of the diacyl lipid phosphatidylcholine (PC) entering the GI tract is absorbed from the upper region of the intestinal lumen where fat-soluble substances are also absorbed. Almost all of this PC is first hydrolysed to form monoacyl lipid. This, together with bile salts, monoacylglycerols and free fatty acids, then form mixed micelles within the lumen which are taken up by intestinal epitheleal cells. Fat-soluble materials such as CyA tend to partition into such micelles and be co-transported across the mucosal membrane. Whilst it is not suggested that the presence of phospholipids employed in the invention actively transport the associated compounds per se across intestinal mucosa, it is likely that absorption of lipids and lipid-soluble compounds take place in parallel. The increased presence of PC and MAPC are likely to improve the bioavailability of CyA.

In sharp contrast to the synthetic ethoxylated surfactants used in earlier formulations, PC and MAPC are endogenous compounds naturally present together in the intestinal mucosa and their presence is likely to be helpful rather than harmful. The mechanism of uptake of CyA from the micelles formed by such detergents is not known but their strong detergency could potentially damage and alter permeability of the mucosa. This may, of course, be one reason why ethoxylated surfactants are used as carriers to promote improved absorption Following transport into the epitheleal cells, the CyA enters the blood-stream where it probably partitions into the lipid components of the high and low density lipoproteins and the membranes of erythrocytes and other cells as hypothesised by Fahr (supra) in the case of direct intravenous injection.

A surprising discovery in this invention is the high solubilising capacity of the lipid mixture when MAPC is present, and the improvement in bioavailability. Furthermore, the physical characteristic of the composition can be a soft wax that can be extruded or a plastic wax that can be broken down into granules or spheronised and presented in unit dosage form. Alternatively, the composition may be presented as a fluid preparation by adding suitable non aqueous hydrophilic or lipophilic media for filling into soft gelatin capsules. The composition may also be dispersed in aqueous media to form aqueous dispersions just before use. With careful control of the phospholipid mixture and processing, the invention could in certain circumstances be suitable for parenteral use after dilution. These unique features also enable it to have other novel uses, such as in inhalation and topical delivery.

In another aspect, the invention provides a lipid carrier composition based on the use of monoacyl phospholpids, preferably in combination with diacyl lipids to solubilise water insoluble, lipophilic compounds and thereby improve their bioavaitablity. The physical characteristics can range from fluid compositions to amorphous wax-like compositions. However, the drug-carrying lipid aggregates formed on dilution with water or other aqueous fluids are organlised lipid aggregates that can be lposomes, mixed micelles or micelles. It should be understood that the type of drug-associated lipid particle(s) obtained is not critical, as long as they have the capacity to cary the lipophilic compound in molecular association and obtain improved bioavailablity. In some instances, where an oil or a lipophilic component is also present, stabilised oil globules may be seen in the heterogeneous suspension at equilibrium.

Embodiments of the invention may overcome two major disadvantages in using liposomes as carriers, namely, physical instability of the vesicles and low entrapment. Unlike liposome preparations, no external aqueous medium is necessary and therefore stability and microbial contamination should not be an issue. Furthermore, expensive and energy intensive equipment is not required to produce liposomes with well defined characteristics. Absence of intensive shearing forces involved in some methods of preparing liposome suspensions avoids the loss of entrapped compound. Furthermore, large scale production is easily undertaken. Although most compounds can be carried in the invention to obtain improved bioavailability, it is particularly suitable for solubilising water-insoluble lipophilic compounds particularly fungal metabolites (e.g. cyclosporiny, and anti-fungal and cytotoxic agents. It may also be useful to deliver peptides and proteins and nucleic acids associated in the form of lipid complexes.

A further unexpected feature of the compositions described is that they will readily disperse into discrete microscopic/colloidal lipid aggregates in the presence of an aqueous fluid, even at room temperature, with minimum agitation. The lipid aggregates obtained on dilution are uniform and mostly in the region of 100 rim when the ratio of diacyl to monoacyl lipid is less than approximately 1:1. Lipophilic compounds remain in association within the aggregates. Depending on the combination of diacyl- to monoacyl lipids and their configuration, the aggregates may be vesicular or non-vesicular. They may be bilayer in form, complexes of bilayers and micetles, or totally micellar. Given the appropriate lipid mixture, the size of the lipid aggregates is unaffected on dispersion in aqueous fluid between the physiological pH range i e. 2 to 8. The monoacyl components both promote solubilisation in the lipid mixture and also aid dispersion into small aggregates in the presence of aqueous medium. Bile salts and other emulsifiers are not essential for release of the compound for absorption in the GI tract as the compound is largely in molecular dispersion in a partially digested lipid mixture. However, as a bonus, dispersion into lipid aggregates may be fuirther improved in the presence of emulsifiers such as bile salts particularly at 37° C.

The present invention can be used to carry different types of compounds for all kind of applications, but it is particularly suitable for carrying lipophitic compounds, especially for oral administration. By way of example, and not by way of limitation the compounds being carried may be CyA and miconazole, an antifiungal compound. In addition to these two examnples of lipophilic compounds, a further example of a highly water insoluble lipophilic compound, astaxanthine is given to demonstrate the utility of the invention in non-pharnaceutical applications. Astaxanthine is widely used in aquaculture to confer pigment to fish, but large amounts have to be given because of poor bioavailability.

It must be understood that these formulations are not limited to the examples shown. Many biologically active compounds eg, peptides, proteins, vaccines, DNA, steroids, hormones, vitamins, anti-arrythinc compounds, etc and other lipophilic compounds can be incorporated in the composition, by selecting the appropriate quantity of lipids, ratio of diayl to monoacyl fractions and cognisant of physical properties of the lipid, such as charge, chain length, degree of saturation and phase transition temperature. The lipid carrier may also be formulated as a fluid composition with appropriate hydrophilic or lipophilic media. Liquid compositions may be more convenient to administer because they can be diluted prior to use or filled into soft gelatine capsules. Solvents used in processing and the presence of residual hydrophilic medium left in the bulk lipid carrier should also be taken into account, as they could affect the association of the compound and bioavailability.

BRIEF DESCRIPTION OF THE DRAWINGS

In the drawings:

FIGS. 1a–1c show schematically micelle-structures resulting from different concentrations of MAPC;

FIG. 2 is a diagram showing the association of CyA vs the MAPC content of the lipid fraction;

FIG. 9 is a diagram showing the association of miconazole and CyA with the lipid;

LIPID AGGREGATES

The present invention is a carrier system that comprises one or more monoacyl lipid or other related micelle forming amphipath, optionally in intimate mixture with bilayer forming diacyl lipid(s). This system is when prepared, normally in the form of an anhydrous (or near anhydrous) solid, waxy solid or liquid and is diluted in aqueous solutions only in use or just prior to use.

Figure 1A:
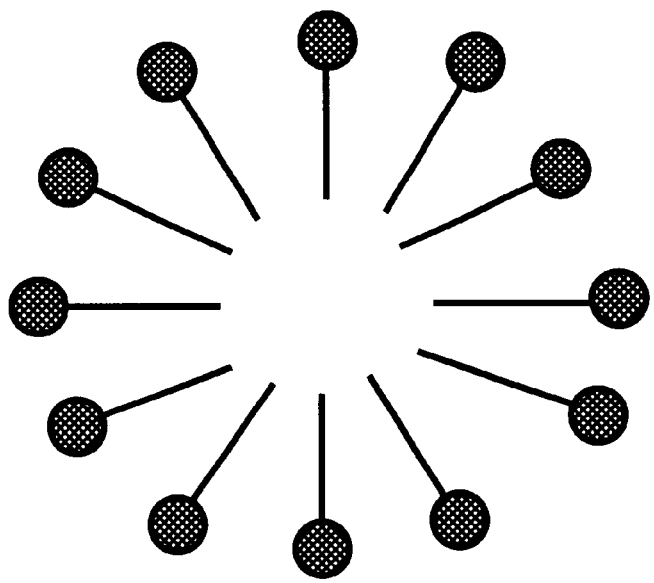
Figure 1B:
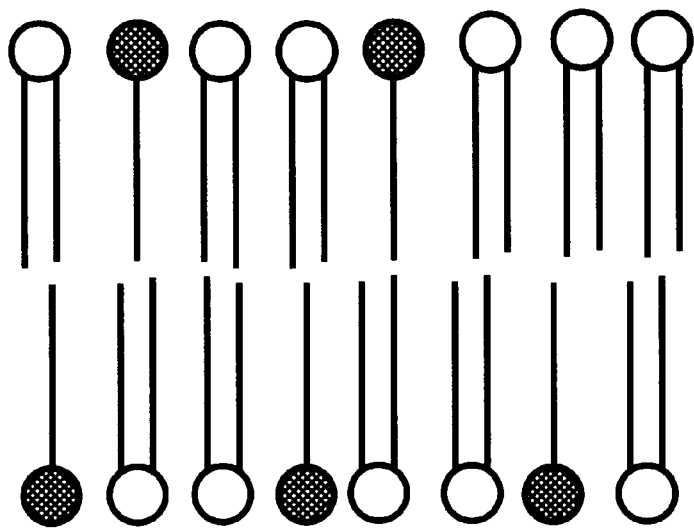

The equilibrium structures formed by PC and MAPC when dispersed in water are fundamentally different. Diacyl PC molecules, which are essentially cylindrical in shape forms conventional lipid bilayers of the type found in liposomes. The monoacyl MAPC molecule, in contrast, has a conical shape and forms spherical micelles of the type normally associated with detergent molecules (FIG. 1a). Dispersions of mixtures of monoacyl and diacyl lipids form intermediate structures. If the content of MAPC is below about 30%, the preferred structure is that of a mixed bilayer (FIG. 1b). At higher concentrations, the preferred structure is that of a mixed micelle (FIG. 1c).

On mixing with aqueous fluids, the carrier system is converted into drug-associated lipid particles which, depending on the ratios of diacyl and monacyl lipids, may be in the form of liposomes, micelles or mixed micelles. At this stage, the lipophilic drug incorporated in the original carrier system may be present in a molecular form intercalated between the lipids making up the lipid aggregates (liposomes or mixed micelles) or held in the form of a totally micellar lipid-drug complex.

Ratio of Diacyl to Monoacyl Lipid

The molar ratio of diacyl lipid to monoacyl lipid, or other micelle forming amphipath, in the mixture may be from 1:99 to 99:1, preferably between 1:25 and 25:1 and most preferably between 1:10 and 10:1 However, it may be necessary to use MAPC alone in some crcumrstances to obtain mwdmum entrapment for compounds that are more difficult to solubilise In such cases, it may be necessary to form micellar associates with MAPC initially. The resultant lipid complex can then either be used as such or mixed in with diacyl lipids.

The monoacyl lipid content in formulations suitable for intravenous use are in the lower region of the preferred range. Monoacyl phospholipids are known to have haemolytic activity but mixtures of diacyl and monacyl phospholipids in the molar ratio of 2:1 have been shown to be non-haemolytic at concentrations up to 1.3 mM in physiological saline. Some polyethoxylated surfactants, in contrast have been reported to produce 100% haernolysis in in vitro tests at concentrations as low as 0.2 mM (Pharm. J. 253, 463 (1994)). It should be borne in mind that although the possibility of haemolysis is an important issue in intravenous use when the injection is given as a bolus, it is much less so in cases of slow IV infusion. However, the use of MAPC is not of concern in oral applications as it is naturally present in the intestinal lumen.

As the proportion of the monoacyl fraction in the lipid mixture increases, the lipid particles formed on equilibrium following dilution, change from typically bilayered, vesicular structures to non-vesicular mixed micellar systems and/or leterogenous mixtures containing different microscopic structures. With 100% monoacyl content, the particles are likely to be totally micellar structures.

The solubilisation capacity for lipophilic compounds also tends to increase with increasing monoacyl lipid content. This is reflected in the results shown in FIG. 2, where the amount of lipid-associated CyA seen in 3:1 w/w lipiddrug formulations is above 40% in formulations in which the lipid fraction contains 20 wt % MAPC. This rises to 100% in formulations containing 80 wt % of MAPC.

Choice of Lipid Components

The diacyl lipid(s) is preferably a phospholipid. Examples of phospholipids are phosphatidylcholine, phosphatidylethanolamine, phosphatidylglycerol, phosphatidylinositol, phosphatidylserine and sphingomyelin. The acyl chain can either be unsaturated or saturated and can have between 12 to 22, preferably 14 to 18 carbon atoms. Other liposome forming membrane lipids such as glycolipids, ceramides, gangliosides and cerebrosides can be used in place of, or partial place of, phospholipids.

The monoacyl lipid(s) is preferably the monoacyl derivative of a phospholipid, but it can also be the monoacyl derivative(s) of glycolipids, sphingolipids, or another suitable micelle forming lipid. The lipids may be derived from natural plant, animal or microbiological sources, synthesised or partially synthesised including polyethyleneglycol (PEG) derived mono-acyl phospholipids, e.g. pegalated mono-acyl phosphatidyl ethanolamine.

In practice, instead of mixing pure fractions of the lipids to obtain the target ratios, partially enzyme-digested mixtures of lecithin that have the required proportions of the diacyl to monoacyl fractions are preferred. These phospholipid mixtures, which are also classed as lecithins, are freely used in foods without restrictions and should thus provide no problems for oral use.

Figure 3:
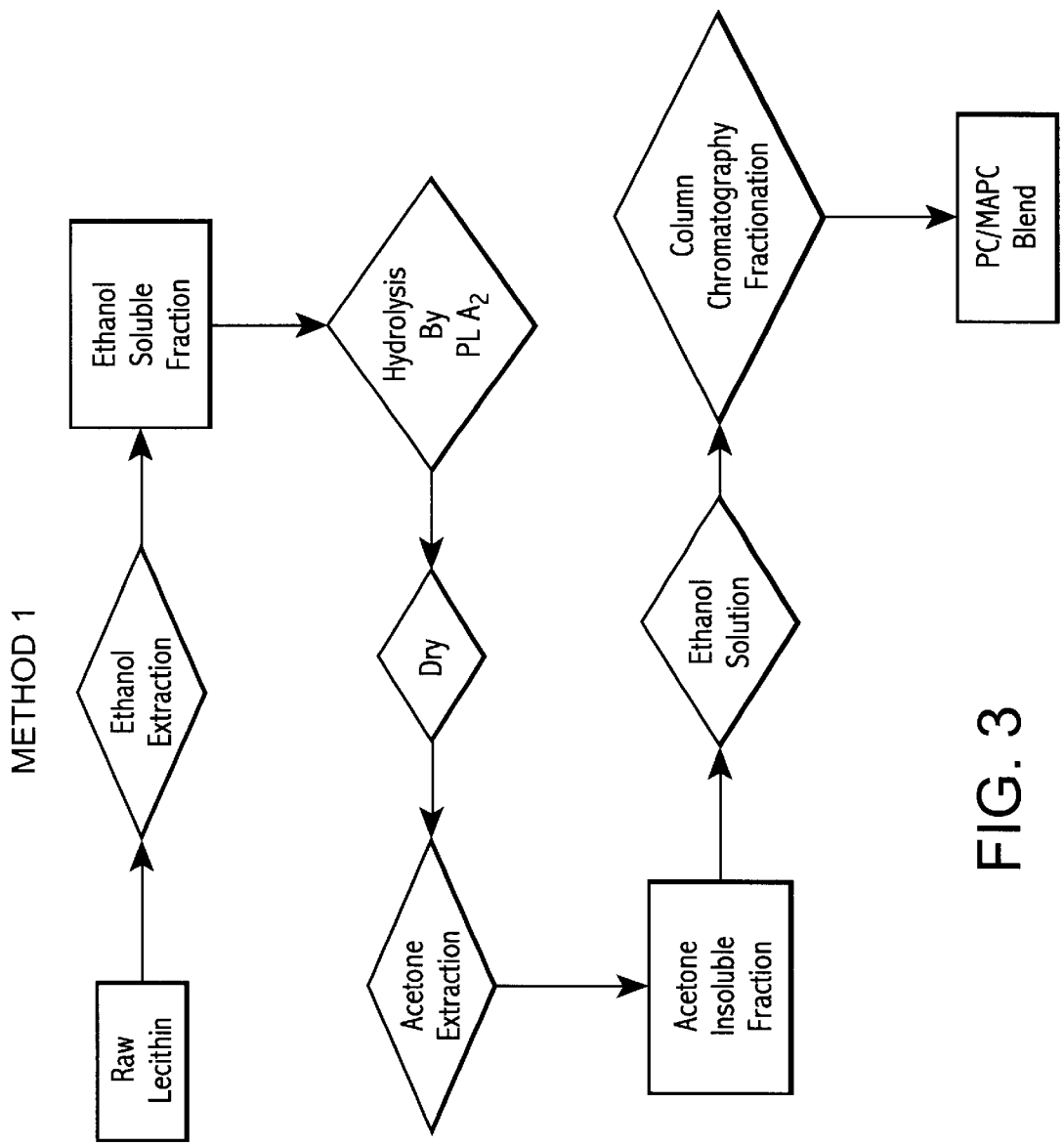
FIGS. 3 and 4 are flow charts for two methods of producing enzyme-modified lipids.
Figure 4:
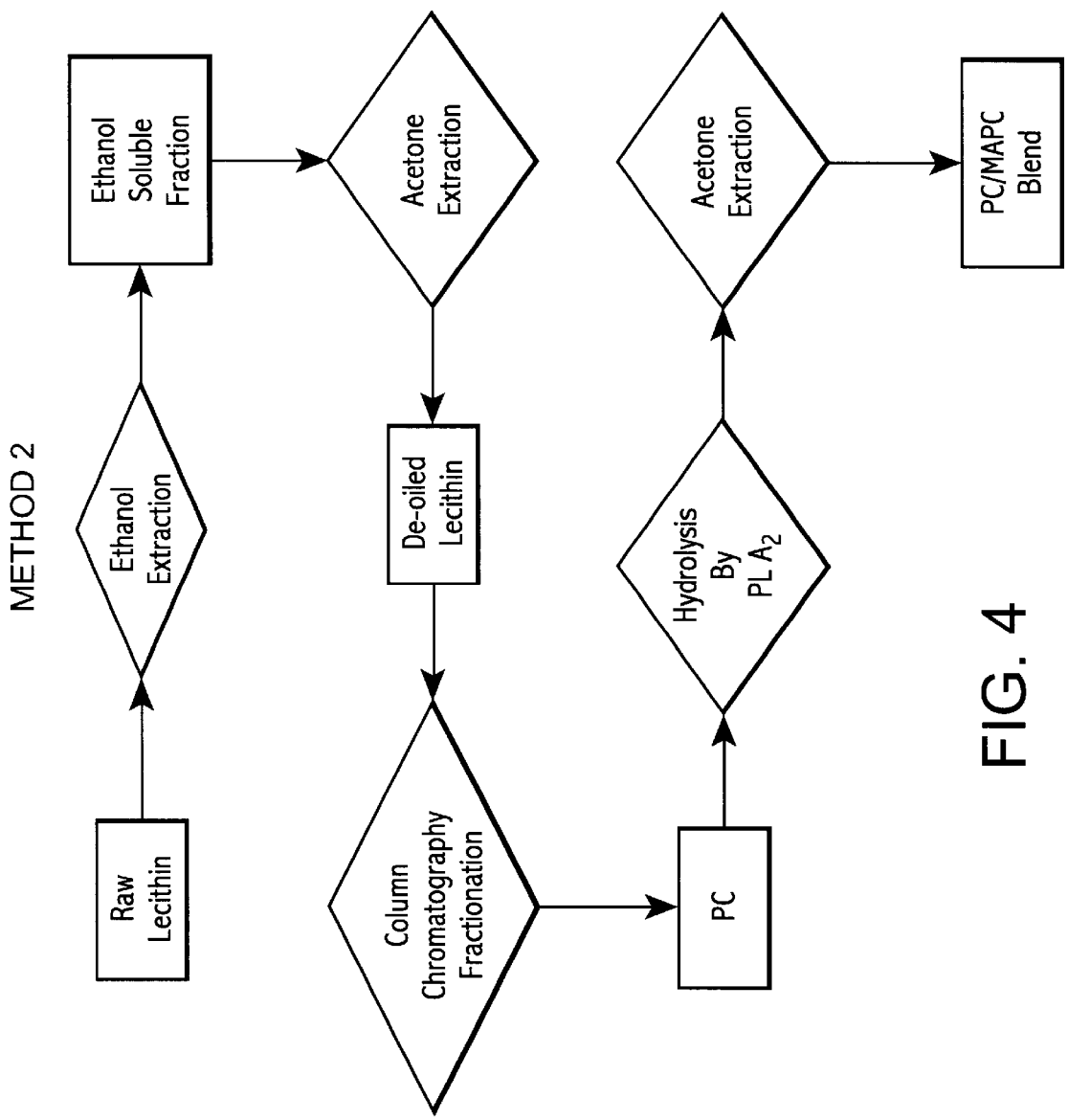

Flow charts for two methods of producing such enzyme-modified lipids based on the enzyme hydrolysis modification of mixtures of diacyl lipids or pure PC by phospholipase A2 are shown in FIGS. 3 and 4. The main difference between the two methods is that in one method the purified mixture containing PC/MAPC is obtained by chromatography in the final step, whereas in the other method, the free fatty acids obtained from hydrolysis are removed by acetone extraction. Methods such as these are sparticularly useful for obtaining blends for use in the present invention. Such blends preferably contain between 20 and 80 mole per cent of monoacyl lipid fraction based on the total phospholipid content.

Drug to Lipid Ratio

The total amount of the lipid mixture required for maximum entrapment will depend on various factors such as, type of lipid, charge, ratio of diacyl to monoacyl fractions and the molecular weight and lipid solubility of the lipophilic compound. Generally, an increase in the monoacyl fraction results in higher association with the compound and less total lipid will be required. This is illustrated in the case of CyA by the results shown in FIG. 5 where increased association can be seen with much smaller amounts of lipid which contain 100% MAPC compared to the use of similar amounts of a lipid blend.

A biologically effective amount of the active compound or compounds should be dispersed in the lipid. The appropriate proportion of biologically active compound to lipid will vary considerably depending upon the potency of the compound, and some compounds which are very potent need be dispersed only in small amounts. The optimum molar ratio of drug or other biologically active compound to lipid therefore varies from application to application but normally lies between 1:1 to 1:50. Ratios of less than 1:1 normally result in very low percentage drug entrapments. Larger amounts of lipid (i.e. drug:lipid ratios<1:50) can, however, be employed without detracting from the invention, particularly. in the case of potent compounds which are effective in very small doses. From practical and cost considerations, the least amount of lipid concomitant with achieving maximal solubilisation and bioavailability, should be employed. This should be readily achievable by careful selection of the diacyl to monoacyl lipid ratio.

Preparation Method

In order to prepare the formulations described in this invention the lipophilic compound is normally used in its molecular form. The best method to achieve this is to dissolve the drug in a suitable solvent first. This solution is then used to solubilise the mixture of lipids. Depending on the lipids employed, a small amount of water, polyol or sugar, may be included to aid dispersion and solubilisation. The amount used need not exceed about 10% by weight. Alternatively, the solution of drug is added to the lipid mixture dispersed or solubilised in a minimal amount of the same or a different solvent. A further method is to allow the lipophilic compound to solubiise in the solution of lipids. This is a much slower process and may be accelerated by maintaining the mixture at an elevated temperature.

In practice, it is convenient to select a solvent that will solubilise or disperse both the lipid mixture and the compound to be carried. Where possible, ethanol is preferred, because it is considered non-toxic for pharmaceutical purposes. However other aliphatic alcohols such as methanol, isopropyl alcohol, propyl alcohol, butanols or volatile hydrocarbons, may be used. Other solvents such as chloroform, dichloromethane solvent, dimethyl formamide (DMF), dimethylsulphoxide (DMSO), tetrahydrofuiran (THF) etc, can also be used in some circumstances to facilitate molecular dispersion of the compound in the lipid, as long as they are carefully removed after processing.

Following dissolution, most if not all of the solvent is removed leaving behind a molecular dispersion of the compound in the lipid mixture. The solvent can be removed by simple rotary evaporation, evaporation under reduced pressure, evaporation on a drum at elevated temperature, spray drying or supercritical extraction, with careful consideration of environmental factors. Spray drying and supercritical extraction would result in the production of a powder formulation. The preferred method is simple evaporation under vacuum at slightly elevated temperature.

Any suitable method can be employed to remove the solvent, provided that given the correct mixture and proportion of lipids in the formulation, the compound remains substantially in molecular dispersion after removal of the solvent. In some cases, depending on the compound, it may be desirable to leave a small amount (1% to 10%) of ethanol or other hydrophilic medium, including water behind. The presence of a small amount of a hydrophilic medium could aid entrapment and could also modify the rheology of the composition to facilitate processing into appropriate dosage forms. The consistency of the final composition can be a fluid or viscous, paste-like material, or it could be turned into a soft or hard wax, depending on the lipid composition and inclusion of other components to modify the rheology and consistency. It is essential that any such excipients should not adversely affect entrapment and performance.

Application to CyA Delivery

The present invention is particularly suitable for the formulation of oral preparations of CyA. Some more specific details relating to such formulations are provided below.

Optimisation of the PC/MAPC Ratio

Lipid-CyA compositions were made with a range of PC APC ratios (20–100% MAPC in PC/MAPC mixture). This was carried out by using the pure PC and MAPC. The samples were prepared by adding 200 mg of CyA to 1.8 gm of different PC/MAPC blends, with the compositions set out in Table 1, in a pre-weighed drying vessel. 2 g of ethanol was added and the composition sonicated in a bath at 50° C. until the solution was optically clear. Ethanol was then removed from the sample under vacuum. The sample was re-weighed at intervals to confirm complete removal of the ethanol. The ethanol-free sample was then transferred to a moisture tight glass container and stored at 4–8° C.

On dispersion in distilled water, the composition spontaneously formed discrete lipid particles, with the lipophilic cyclosporin entrapped in the complex. The percentage association of the cyclosporin was assayed by filtration of the lipid dispersion through 200 nm filters. The principle behind the filtration technique is that the aggregates (with associated cyclosporin) can be passed, while unassociated drug particles are too large to pass through the filters. The percentage association of the cyclosporin (in 2% suspensions of the formulations) measured immediately after sample preparation are listed in Table 1.

TABLE 1

The effect of PC/MAPC ratio on the association of CyA using lipid/drug ratios of 3:1, 4:1, 6:1 and 9:1.

| Formulation | Association |
| --- | --- |
| Lipid blend 80:20 w/w PC:MAPC | |
| Lipid: Drug: | |
| 3:1 w/w | 42.9% |
| 4:1 w/w | 63.3% |
| 6:1 w/w | 98.7% |
| 9:1 w/w | 99.0% |
| Lipid blend 50:50 w/w PC:MAPC | |
| Lipid: Drug: | |
| 3:1 w/w | 85.8% |
| 4:1 w/w | 99.2% |
| 6:1 w/w | 99.9% |
| 9:1 w/w | 98.9% |
| Lipid blend 0:100 w/w PC:MAPC | |
| Lipid: Drug: | |
| 3:1 w/w | 99.3% |
| 9:1 w/w | 99.6% |

Fuller results obtained for the 3:1 and 9:1 lipid drug ratio samples are shown in FIG. 4 which shows the effect of changing MAPC content on CyA association. They clearly demonstrate that incorporation of higher proportions of MAPC leads to marked increases in the amounts of CYA that can be successfully incorporated into the formulations.

Lipid blends with MAPC levels greater than 60 wt % were found to produce clearer dispersions of cyclosporin on dilution, indicating micelle formation in addition to, or in place of, liposomes. In practice, lipid blends containing between 60 to 80 mol per cent of MAPC based on the total phosphatides, obtained by enzyme hydrolysis with phospholipase A2 are preferred.

Figure 5:
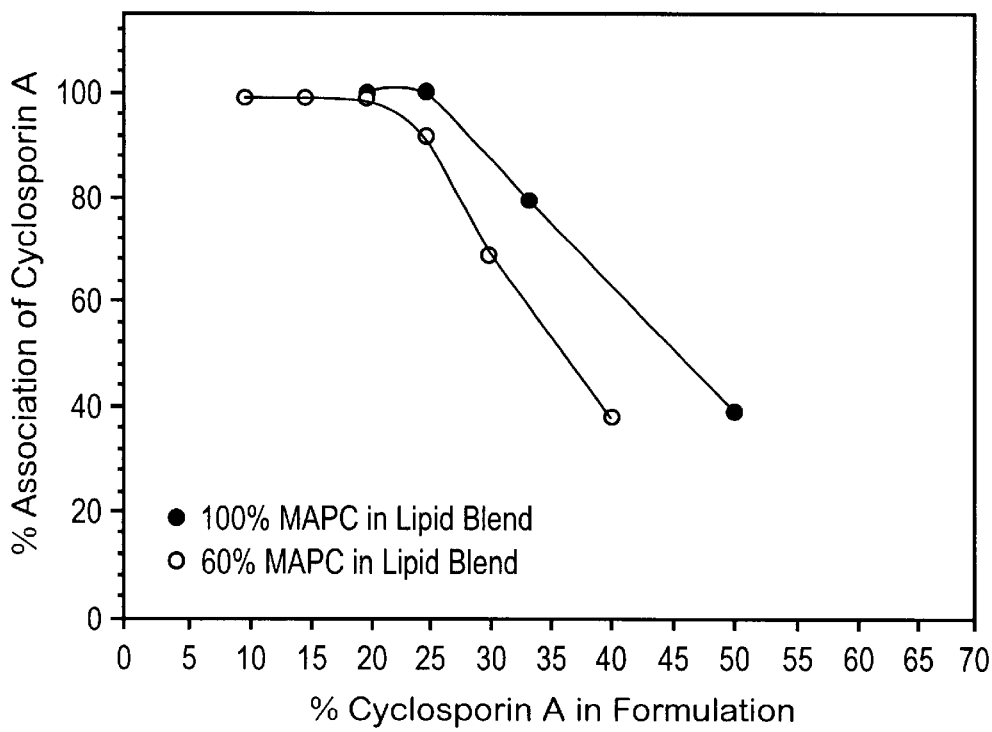
FIGS. 5 and 6 are diagrams to illustrate the CyA to lipid ratio depending on different MAPC contents.

The general dependence of association efficiency on MAPC levels is further illustrated in FIG. 5 which compares the extent of association in lipid blends containing 60% and 100% w/w MAPC.

Optimisation of the Lipid/Drug Ratio

Figure 6:
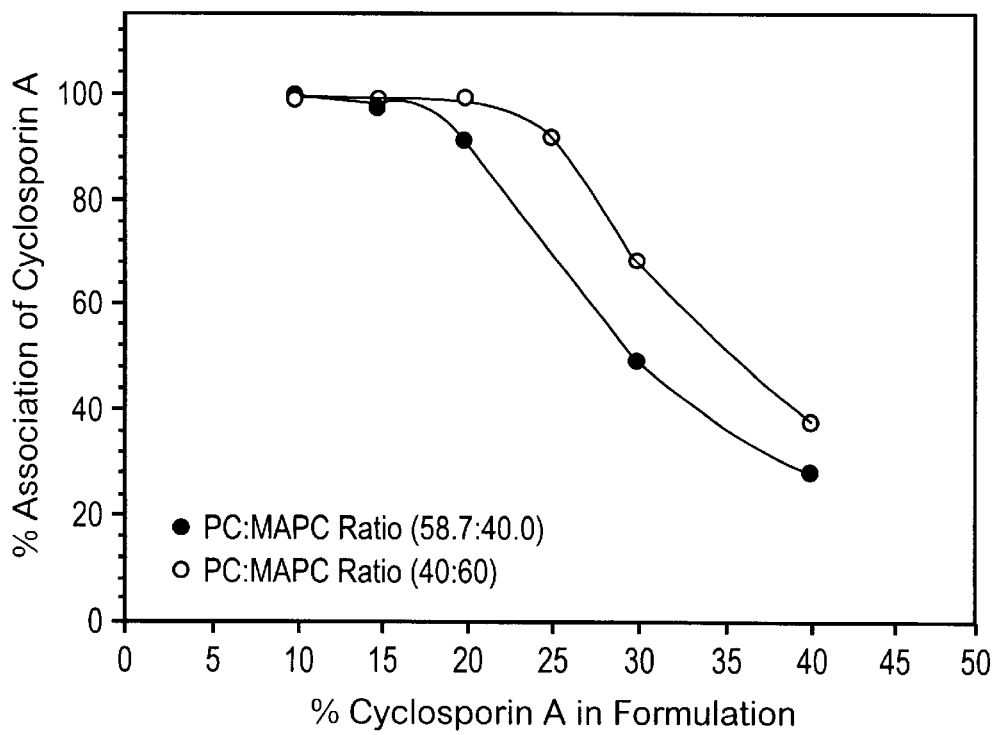

A series of Lipid-CyA formulations were also made with two fixed lipid compositions and varying lipid/drug ratios. The percentage association of the CyA in 2% suspensions of the formulations was measured immediately after preparation as described above. The results, which are shown in FIG. 6, again demonstrate the increased association of the drug at higher MAPC contents.

Use of Enzyme-modified PC

The measurements described above were repeated using pure MAPC blended with pure PC. Measurements were also carried out using an enzyme-modified lipid blend prepared using phospholipase A2 (EML) which contained 39 wt % PC, 52 wt % MAPC and 9 wt % free fatty acids. The association results from these measurements are listed in Table 2.

TABLE 2

The effect of lipid/drug ratio on the association of CyA using enzyme-modified PC.

| Formulation | Association |
| --- | --- |
| EML Lipid (10 wt % CyA) | 99.6% |
| EML Lipid (15 wt % CyA) | 99.9% |
| EML Lipid (20 wt % CyA) | 99.7% |
| EML Lipid (25 wt % CyA) | 86.6% |
| EML Lipid (30 wt % CyA) | 62.8% |

The association efficiency of the enzymically modified PC was very similar to that shown for the 60 wt % MAPC sample prepared using pure PC and MAPC shown in FIG. 2 demonstrating the suitability of these modified PC samples for use in the present invention.

Electron Microscopy and Particle Sizing Studies

Figure 7A:
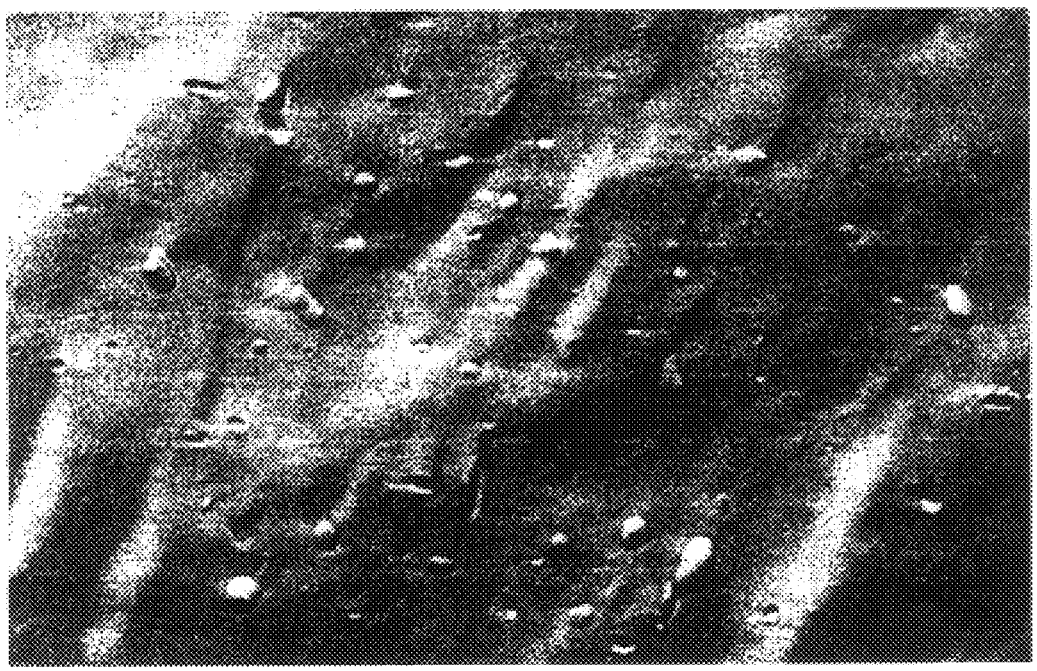
FIGS. 7a–7c are Electron Microscope photographs of liposomes formed in destined water.
Figure 7B:
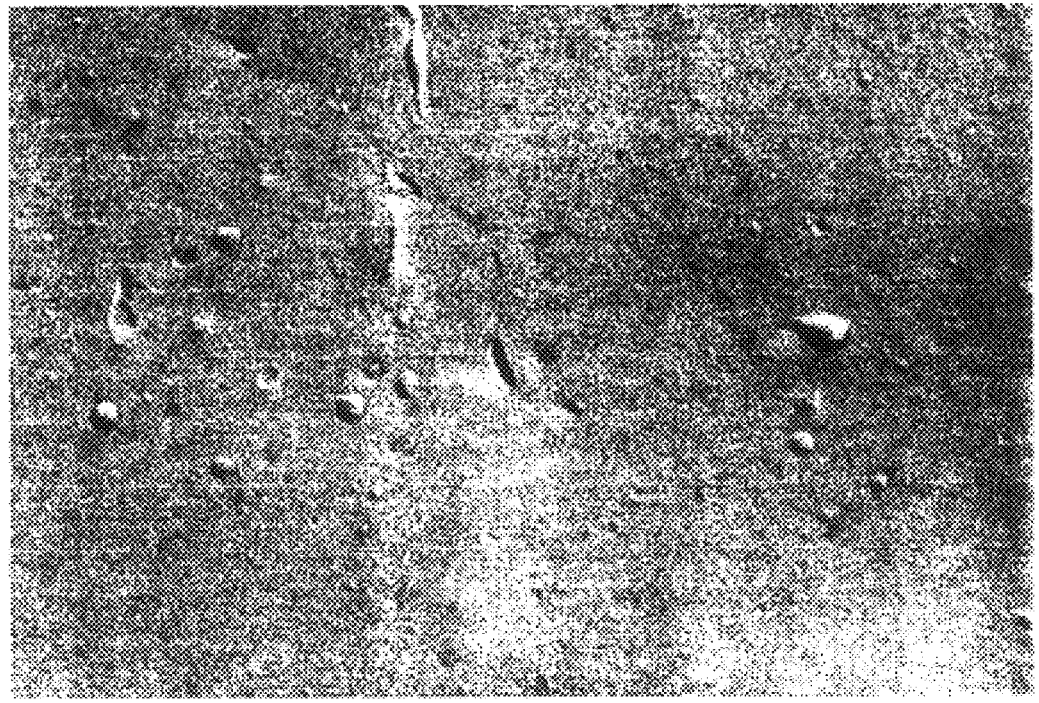
Figure 7C:
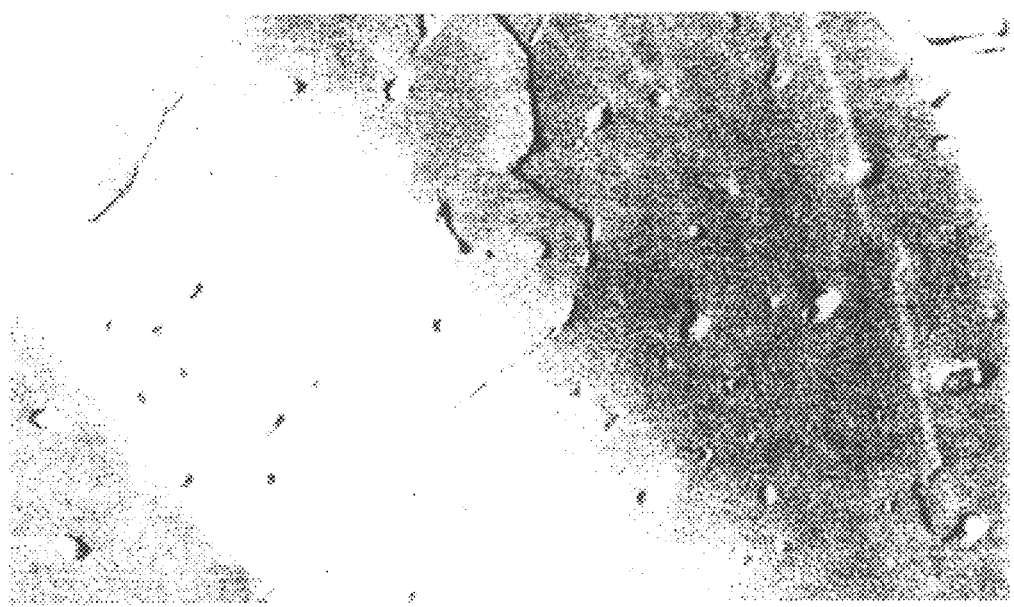
Figure 8A:
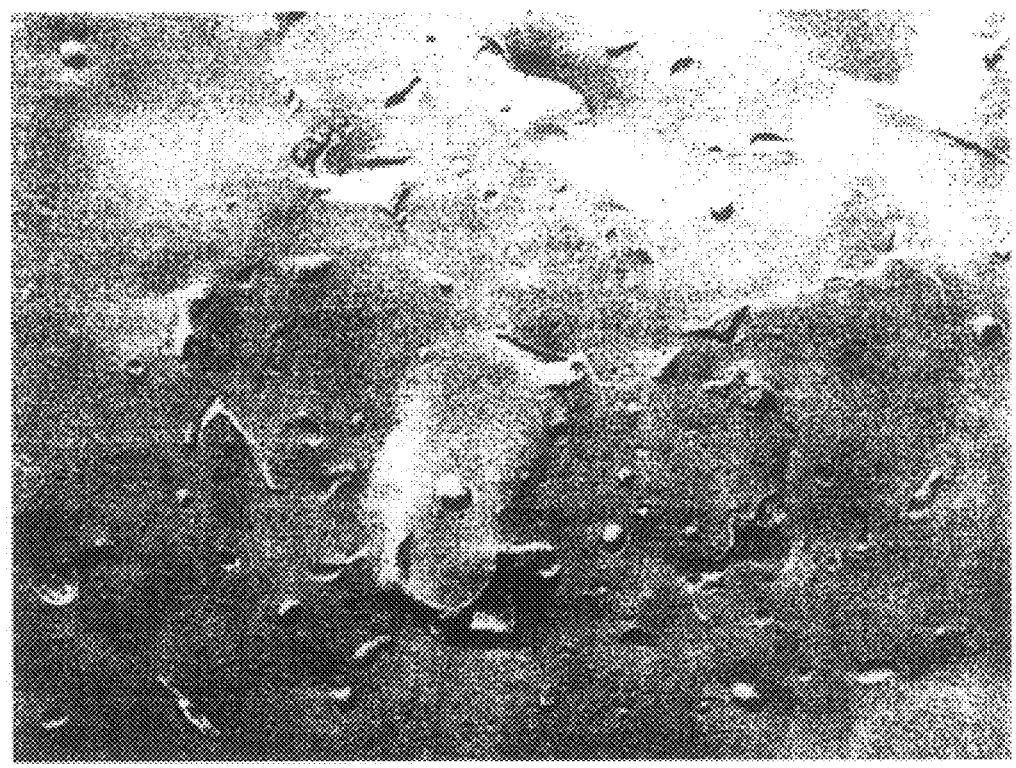
FIGS. 8a–8c are Electron Microscope photographs of liposomes formed in gastric fluid.
Figure 8B:
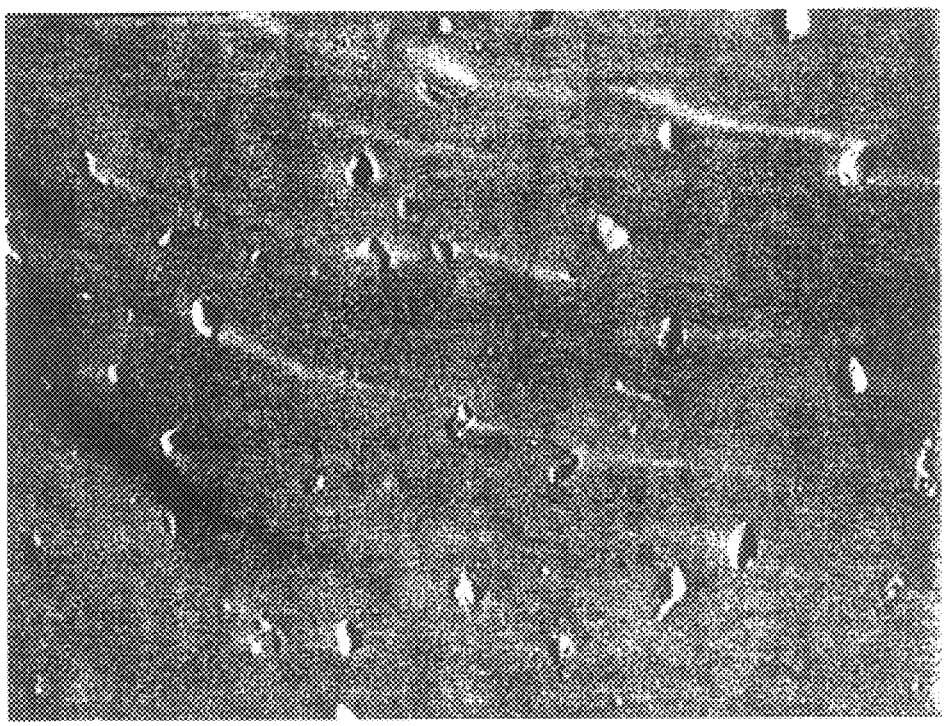
Figure 8C:
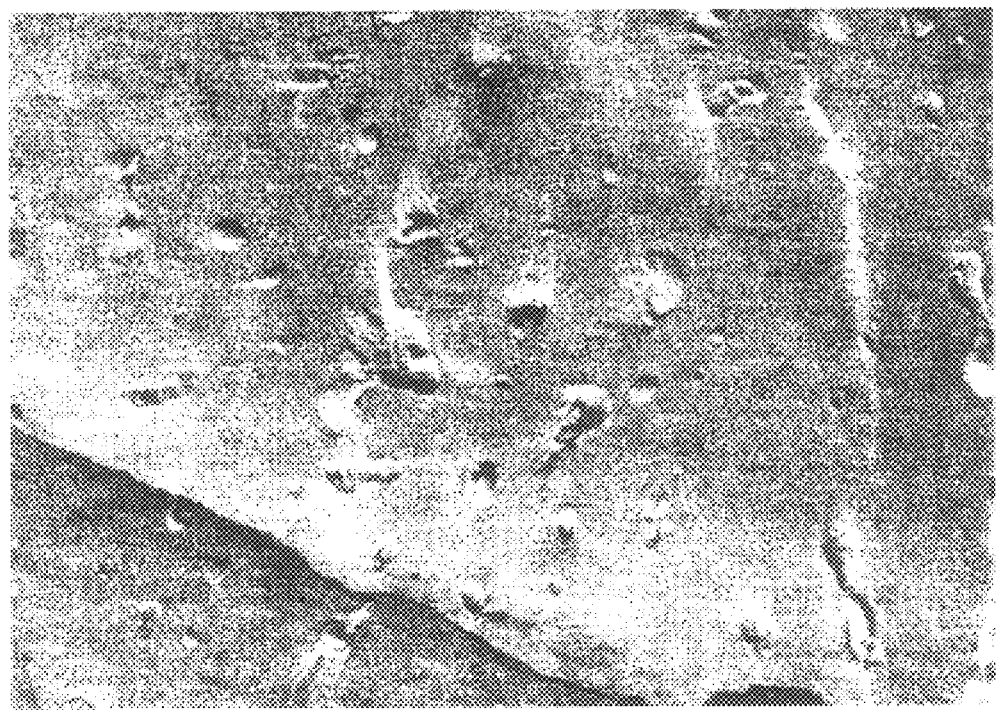

The presence of vesicular structures produced by the CyA-lipid formulations when diluted in either water or gastric fluid, was determined by freeze-fracture electron microscopy. Typical freeze-fracture electron micrographs of 9:1 w/w lipid drug samples prepared using (a) 60:40 (b) 50:50 and (c) 40:60 w/w PC:MAPC diluted in water and artificial gastric fluid, are shown in FIGS. 7 and 8. respectively. FIG. 7 is a freeze fracture electron micrographs of lposomes formed in distilled water a) PC:MAPC 60:40 w/w magnification ×28,000, b) PC:MAPC 50:50 w/w magnification ×59,000, c) PC:MAPC 40:60 w/w magnification ×28,000. All samples had lipid:drug ratios of 9:1 W/W and were diluted to a final lipid concentration of 2 wt %. FIG. 8 is a freeze fracture electron micrographs of liposomes formed in gastric fluid a) PC:MAPC 60:40 w/w magnification ×28000, b) PC:MAPC 50:50 w/w magnification ×43,000, c) PC:MAPC 40:60 w/w magnification ×43,000. All samples had lipid;drug ratios of 9:1 w/w and were diluted to a final lipid concentration of 2 wt %.

Unilamellar liposomes with a diameter of approximately 100 nm are clearly visible in both systems. The size of the drug-lipid aggregates were also determined by a dynamic light scattering technique (photon correlation spectroscopy) using a Malvern Autosizer. The results of these measurements, listed in Table 3, also indicated that the lipid-drug aggregates had an average diameter of around $100 \geq 200$ nm.

TABLE 3

Particle Size Of Lipid Aggregates In Gastric Juice And Water

| Sample | Medium | Lipid Aggregate Particle Size | Appearance of Lipid Aggregate Dispersion |
|---|---|---|---|
| 1 - PC:MAPC (60:40)** | Water | 161 ± 110 nm | Medium thick and milky |
| 2 - PC:MAPC (50:50)** | Water | 188 ± 139 nm | Medium thick and slightly milky |
| 3 - PC:MAPC (40:60)** | Water | 150 ± 120 nm | Thick and slightly milky |
| 1 - PC:MAPC (60:40)* | Gastric Fluid | 227 ± 177 nm | Medium thick and milky |
| 2 - PC:MAPC (50:50)** | Gastric Fluid | 127 ± 69 nm | Medium thick and slightly milky |
| 3 - PC:MAPC (40:60)** | Gastric Fluid | 113 ± 54 nm | Thick and slightly milky |

*Enzyme modified phospholipid
**Pure mixtures

Similar sized liposomes were seen with diluted formulations, one made with the enzyme-modified lipid having about 65% MAPC. In general, compositions containing more than about 70% MAPC tend to be somewhat transparent suggesting the presence of micellar structures. Some vesicular structures can still be observed by electron microscopy but the method is too insensitive to allow the direct visualisation of spherical micelles.

The invention will now be further described with reference to the accompanying examples.

EXAMPLE 1

100 g of PC, MAPC, CyA(M. Wt 1202) in the molar ratios 10:7:1 was added to 50 gm of absolute ethanol and allowed to solubilise in a closed vessel to give an optically clear solution. The mixture of lipid was obtained by enzyme hydrolysis. Solution was achieved by stirring the mixture at room temperature. The absence of crystalline material was confirmed by passing the material through a 200 nm pore size Cyclopore filter and, examining the filter for crystals of the drug.

Ethanol was then removed from the resulting solution to give an intimate mixture of the CyA and the bilayer lipids. Ethanol removal was under moderate heating and vacuum assisted until gravimetric estimation revealed less than 1% of ethanol. The resultant lipid/CyA composition was a soft wax-like gel and contained 100 mg of drug in 1000 mg of sample. It was filled into gelatine capsules containing 100 mg of CyA in each capsule.

EXAMPLE 2

A mixture of 100 g PC, MAPC and CyA in the molar ratios 28:2:1 was dissolved in 75 g of ethanol in a closed container to obtain a homogenous solution, as in Example 1. The required ratio of PC/MAPC in the blend was obtained by adding pure PC to the blend used in Example 1. The resultant lipid composition following removal of the ethanol was a viscous paste. A small quantity of glycerol was mixed in with the paste-like material and worked in, to turn it into a less viscous gel. This CyA lipid composition was filled into soft gelatine capsules. Each capsule contained 50 mg of CyA in association with the lipid.

EXAMPLE 3

A mixture of 100 g of PC, MAPC and CyA in the molar ratios 5:5:1 was dissolved in 100 g of ethanol in a closed container as described in Example 1. The mixture of lipid was obtained by blending PC and PC/MAPC mixtures as in Example 2. The resultant lipid composition following removal of the ethanol was a soft wax. A small quantity of triglyceride (miglyol) was blended into the composition to lower its viscosity and facilitate filling into gelatine capsules. In practice, it was often found to be more convenient to add excipients of this type to the ethanolic solution of the components prior to solvent removal.

EXAMPLE 4

A composition containing 100 g PC, phosphatidylethanolamine, phosphatidyl inositol, MAPC, and CyA in the molar ratios 10:7:3.5:1:1 was dissolved in 75 g of ethanol under gentle heat, with stirring, as in Example 1 until no crystals of CyA could be detected. The ethanol was removed under vacuum until a clear gel was obtained. The resultant CyA lipid mixture obtained contained >5% ethanol. This was filled into gelatine capsules each containing 50 mg CyA.

EXAMPLE 5

10 gm of CyA was dissolved in about 50 gm of ethanol by sonication. The solution was added to 90 gm of a 60/40 w/w, PCIMAPC blend obtained by enzyme modification. The mixture was sonicated in a water bath at about 45° C. until a homogeneous solution was obtained. A CyA-lipid complex was formed by ethanol evaporation as in Example 1. This formulation was used to compare bioavailability against the comparator product (Neoral) in dogs. 500 mg of the lipid complex was filled into hard gelatine capsules (size 0), each containing 50 mg CyA.

EXAMPLE 6

500 mg of CyA was solubilised in about 5 ml of ethanol. 4.5 gm of a 30/70 w/w mixture of pure PC/MAPC was added to the ethanol solution. A CyA-lipid complex was formed by ethanol evaporation as in Example 5. The composition was administered to rats using 5 mg/kg body weight, in gelatine capsules.

EXAMPLE 7

The procedure of Example 6 was followed to produce 5 gm of a CyA-lipid complex, employing a 60/40 w/w blend of a pure PCIMAPC mixture. The composition was used in the same rat study carried out with Example 6, to evaluate bioavailability against the comparator.

Modification of the lipid-cyclosporin Formulation

The most appropriate formulation approaches for filling into hard gelatin capsules are flowable powders or extrudable compositions. Work was undertaken to alter the physical characteristics of the soft waxy composition obtained in the aforementioned examples, by incorporating various excipient materials into the compositions shown below.

EXAMPLE 8 TO 29

Method: In each case, 1 gm of the excipient under evaluation was included in 800 mg of enzyme modified lipid (EML). 200 mg of CyA was added, followed by about 2 gm ethanol. The lipid cyclosporin complex was obtained following the evaporation procedure as in Example 1.

TABLE 4

Composition and characteristics of cyclosporin formulations incorporating ~50% of various excipients. The lipid mixture used was obtained by enzyme modification (EML).

| Chemical (Example No) | Sample Appearance | Hydration time (Hrs) |
| --- | --- | --- |
| Cetyl palmitate (8) | sticky white powder | 5–6 |
| Saccharose mono-distearate (9) | dry ivory powder | 1–2 |
| Saccharose monopalmitate (10) | dry ivory powder | 1–2 |
| PEG-32 glyceryl laurate (11) | yellow solid | |
| PEG-32 glyceryl palmito stearate (12) | yellow solid | 12–24 |
| PEG-32 glyceryl stearate (13) | yellow solid | >24 |
| PEG-6 glyceryl mono-oleate (14) | yellow solid | 5–6 |
| Propylene glycol laurate (15) | yellow solid (non-homogenous) | 5–6 |
| Poloxamer 188 (16) | ivory solid - easy to break up | 1–2 |
| Poloxamer 407 (17) | ivory solid - easy to break up | 1–2 |
| PEG 3350 (18) | ivory solid - easy to break up | 5–6 |
| Glyceryl monostearate (19) | yellow solid | >24 |
| Glyceryl monodicocoate (20) | hard yellow solid | >24 |
| Glyceryl monostearate/citrate (21) | hard yellow solid | 12–24 |
| Propylene glycol dicaprylate/caprate (22) | very thick liquid/solid | 1–2 |
| Polyoxol 40 stearate (23) | yellow solid | 5–6 |
| Glycerol (24) | yellow solid | 1–2 |
| Polysorbate 80 (25) | yellow solid (non-homogenous) | 1–2 |
| Sorbitan trioleate (26) | soft thick yellow liquid | <1 |
| Ethyl oleate (27) | soft thick yellow liquid | <1 |
| Isopropyl myristate (28) | soft thick yellow liquid | <1 |
| Control (29) | Yellow solid | 5–6 |

The physical characteristic of the lipid composition was altered by incorporating a variety of different excipients into the formulation. The hydration time required to form the lipid aggregates varied according to the type of excipient and the amount used. Although 50% by weight of each excipient was used in the examples, this is not a strict requirement. Quantities smaller or larger may be employed to alter the physical characteristics and dissolution profiles of the lipid compositions. The association of cyclosporin may be reduced in some of the formulations. PEG 3350 and Poloxamer 188 did not reduce cyclosporin association and made the formulation more friable. These materials, which function as hydrophilic vehicles, are useful in making an extrudable composition. Solid, lipid-cyclosporin compositions suitable for processing into granules or spheres for filling into hard gelatin capsules and other solid unit dosage forms can also be obtained in this way.

EXAMPLE 30

The lipid composition obtained from Example 18 with PEG 3350 was cooled using dry ice and then comminuted in a mortar and pestle. The sample ground easily to give a flowable powder that could be filled into hard gelatine capsules. At room temperature, the sample still remained powdered inside the capsule.

EXAMPLE 31

This is an example which includes hydrophilic medium to form a viscous lipid-cyclosporin composition suitable for filling into hard gelatin capsules.

1400 mg of a 60/40 w/w PC/MAPC enzyme modified lipid blend and 200 mg of CyA was solubilised in 400 mg of propylene glycol and about 2000 mg of ethanol. Ethanol was removed from the solution of CyA in lipid as in Example 1 to form a viscous lipid-CyA complex containing 100 mg of CyA in 1 gm. The composition dispersed with minimum agitation and forms lipid-CyA aggregates in aqueous medium with over 99% association of CyA.

EXAMPLE 32

This is an example which includes a lipophilic medium to obtain a liquid lipid-CyA composition suitable for filling into soft gelatine capsules.

4 gm of a lipid blend comprising 40/60 w/w pure PC/MAPC, 1 gm of CyA was dissolved in a solution containing 1.25 gm ethanol 1.25 gm glycerol and 2.5 gm propylene glycol monolaurate at about 45° C. A clear solution containing 10% CyA was obtained that was suitable for filling into soft gelatin capsules.

It will be appreciated that the capsules may be of any non-toxic physiologically acceptable material, and that there is at present intensive researcg aimed at finding suitable substitutes for gelatin. Instead of gelatin, other suitable materials may be used to avoid the use of animal derived materials.

EXAMPLE 33

This example illustrates the preparation of a lipid-miconazole complex. An enzyme modified lipid mixture containing 60/40 w/w PC/MAPC was used. 2 gm of the sample was prepared by completely solubilising 200 mg of miconazole in about 1 gm of ethanol as in Example 5. 1.8 gm of lipid was added and the lipid complex was formed following the method described in Example 1.

For comparison, the association of miconazole and CyA with the lipid is shown in FIG. 9. Association of miconazole, using the 60/40 w/w enzyme hydrolysed PC/MAPC blend follows a similar trend to CyA. The % w/w association is less for miconazole reflecting the smaller molecular weight of miconazole.

EXAMPLE 34

This is an example using a carotenoid that is poorly soluble in water. In place of ethanol, tetrahydrofurol was used to solubilise the astaxanthine.

5 mg of astaxanthine and 95 mg of the 40/60 w/w PC/MAPC lipid mixture used in Example 33 were dissolved in about 5 ml of tetrahydrofurol. The mixture was heated at 40° C. until the lipid and astaxanthine had dissolved. The solvent was removed under vacuum and slight heat. A homogeneous complex was formed. The complex was examined for signs of unassociated astaxanthine which would show up as purple crystals. The suspension of lipid aggregates formed in water was subjected to analytical filtration to determine the amount of unassociated astaxanthine. Approximately 98% of astaxanthine was found to be lipid associated using the 40/60 PC/MAPC lipid mixture.

EXAMPLE 35

The procedure in Example 34 was repeated, using 5 mg of astaxanthine in 95 mg of a 99/1 w/w PC/MAPC lipid mixture in place of the 60/40 blend. In this case, less than 50%/a astaxanthine was found to be associated with the lipid containing 1 part of MAPC.

Figure 10:
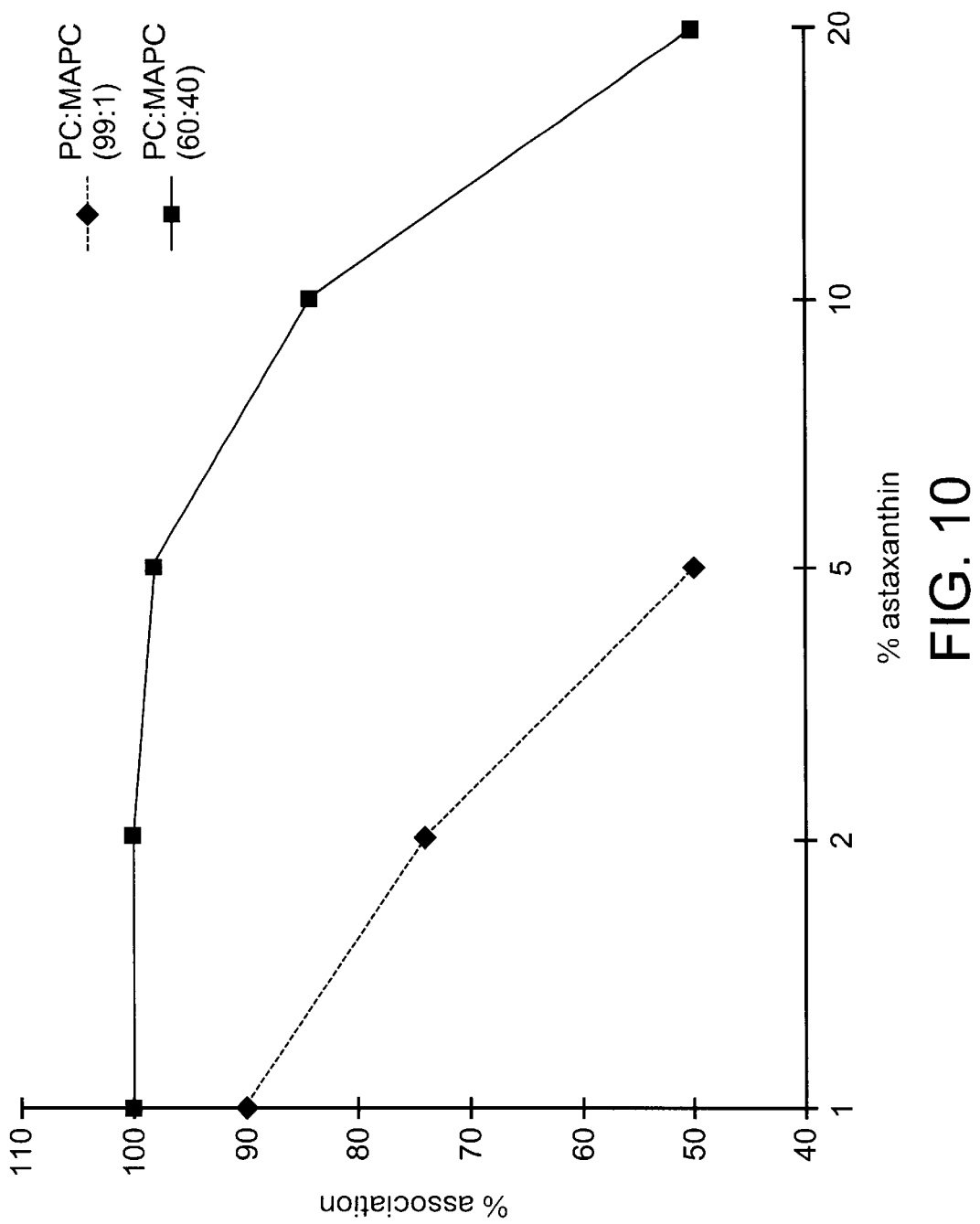
FIG. 10 is a diagram showing the association of astaxanthine using mixtures of lipids of varying PC/MAPC ratios.

The association of astaxanthine using mixtures of lipid with 60/40 and 99/1 (w/w) PC/MAPC is shown in FIG. 10. It confirms that the amount of MAPC in the lipid blend increases the association of water insoluble lipophilic compounds.

Stability Data

Table 5 sets out the stability of a lipid-cyclosporin composition prepared with 10% cyclosporin / 90% lipid (60/40 PC/MAPC) according to Example 5. The samples were placed on storage at 4° C., 25° C./60% RH and 40° C./75% RH.

TABLE 5

Storage stability of lipid-cyclosporin formulation.

| % Cyclosporin Remaining | 4° C. | 25° C./60% RH | 40° C./75% RH |
| --- | --- | --- | --- |
| Initial | 100.6% | | |
| 1 month | 101.4% | 101.8% | 98.4% |

| % Cyclosporin Association | 4° C. | 25° C./60% RH | 40° C./75% RH |
| --- | --- | --- | --- |
| Initial | 98.9% | | |
| 1 month | 99.6% | 99.0% | 99.6% |

It can been seen that there were no significant changes in the % cyclosporin remaining or the % cyclosporin association.

Bioavailability

Figure 11:
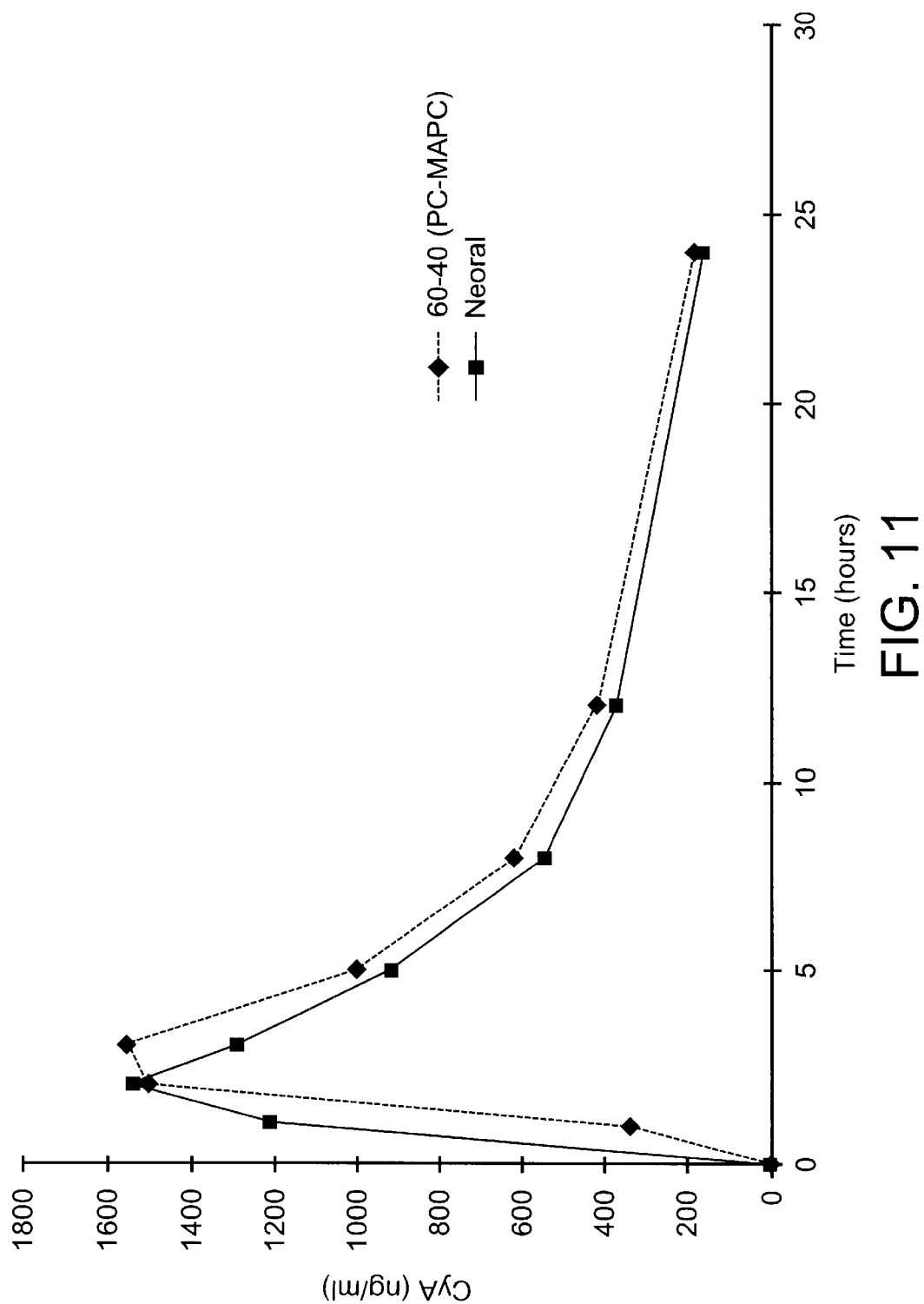
FIGS. 11 and 12 show blood concentrations of CyA vs time after a single administration of different compositions in accordance with the Examples to test animals.

CyA lipid formulations as described above are expected to be bioequivalent to Neoral, without having to rely on potentially harmful surfactants with detergent properties. To evaluate the bioavailability, compositions prepared according to Examples 5, 6 and 7 of the invention, were administered to two animal species as a single dose. FIG. 11 shows the blood concentration (ng/ml) of CyA after single administration of the composition prepared according to Example 5, over a period of 24 hours in a total of 9 fasted beagle dogs. The amount of CyA administered in each case was 100 mg contained in 2×500 mg gelatine capsules with 50 mg CyA in each capsule. Blood samples were taken from the fore-legs after 1, 2, 4, 6, 8, 12 and 24 hours post administration and assayed for CyA using a non-specific radioimmune assay (RIA). The blood concentration of CyA obtained with the comparator (Neoral) is also shown on the same graph. It can be seen that the maximum concentration of CyA in the blood (Cmax) after 4 hrs was somewhat higher with the lipid-CyA complex from Example 5 than Neoral, whilst the total amount of CyA absorbed represented by the area under the curve (AUC) was also slightly higher.

Figure 12:
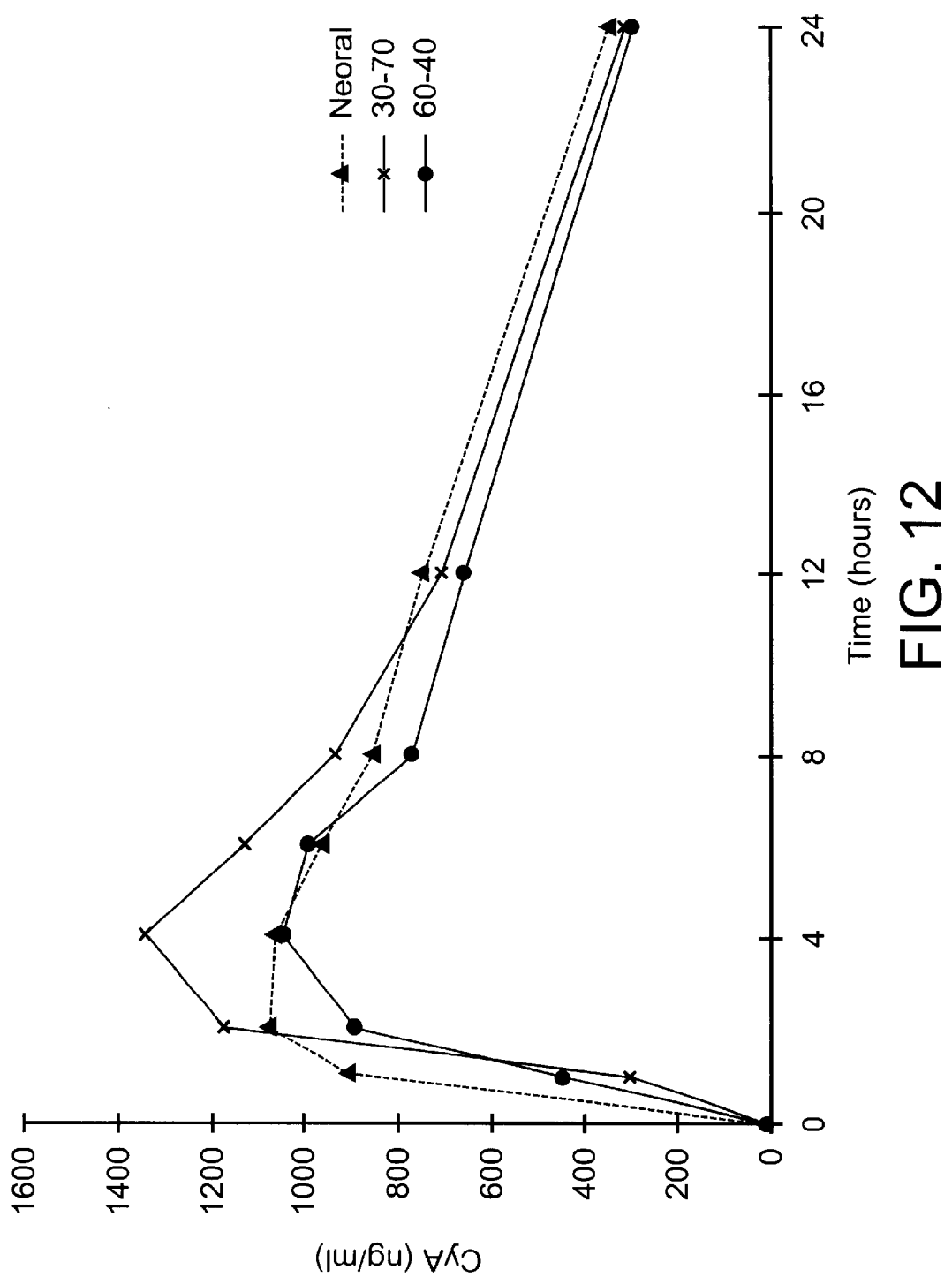

A similar pattern can be seen in FIG. 12, which plots the blood concentration of CyA against time in a similar study carried out in Wistar rats, following administration of a single dose (5 mg/kg) of the lipid-cyclosporin composition described in Examples 6 and 7. A total of 10 rats was used in each study and blood samples were taken from the tail and assayed for CyA using a specific RIAn for rats.

By suitable selection/of the PC/MAPC content, a lipid-CyA composition that is bioequivalent to Neoral can be obtained. Advantageously, these formulations make use of natural lipid components according to the invention, to solubilise and deliver therapeutic concentrations of the lipophilic drug CyA, predictably and effectively. The invention provides a natural carrier of compounds that are poorly water-soluble and should, therefore, have wide-ranging pharmaceutical and other applications.

What is claimed is:

1. A method for delivering a biologically active lipophilic compound to a living organism, which comprises administering orally to said organism a substantially homogeneous composition comprising said biologically active lipophilic compound, a blend of at least one diacyl phospholipid and at least onto monoacyl phospholipid which is derived from a partial enzyme digestion of diacyl phospholipids, said blend having a monoacyl phospholipid:diacyl phospholipid molar ratio of between 1:10 and 10:1, and said monoacyl phospholipid being a micelle-forming lipid,and not more than 10% by weight of water, the lipophilic compound being dissolved in or associated with said blend, wherein upon contact with aqueous fluid said composition spontaneously forms discrete lipid aggregates, which aggregates together with said associated biologically active lipophilic compound are sized to pass through a 200 nm pore size filter.

2. The method of claim 1, wherein the organism is a human.

3. The method of claim 1, wherein the compound is hydrophobic neutral cyclic.

4. The method of claim 1, wherein the compound is cyclosporin.

5. The method of claim 1, wherein the compound is astaxanthin.

6. A substantially homogeneous composition for delivering a biologically active lipophilic compound orally to a living organism, said composition comprising a blend of at least one diacyl phospholipid and at least one monoacyl phospholipid said blend being derived from a partial enzyme digestion of diacyl phospholipids and having a monoacyl phospholipid:diacyl phospholipid molar ratio of between 1:10 and 10:1, and said monoacyl phospholipid being a micelle-forming lipid, not more than 10% by weight of water, and a biologically effective amount of said biologically active lipophilic compound being associated with said blend, wherein upon contact with aqueous fluid said composition spontaneously forming discrete lipid aggregates, which aggregates together with said associated biologically active lipophilic compound are sized to pass through a 200 nm pore size filter.

7. The substantially homogenous composition of claim 6, wherein said biologically effective amount of said biologically active lipophilic compound is at least partially dissolved in said blend.

8. A composition for delivering a biologically active lipophilic compound orally to a living organism, said composition comprising a blend of at least one diacyl phospholipid and at least one monoacyl phospholipid said blend being derived from a partial enzyme digestion of diacyl phospholipids and having a monoacyl phospholipid:diacyl phospholipid molar ratio of between 1:10 and 10:1, and said monoacyl phospholipid being a micelle-forming lipid, not more than 10% by weight of water, and a biologically active lipophilic compound being associated with said blend, wherein upon contact with aqueous fluid said composition spontaneously forming discrete lipid aggregates, which aggregates together with said associated biologically active lipophilic compound are sized to pass through a 200 nm pore size filter.

9. The substantially homogenous composition of claim 8, wherein said biologically effective amount of said biologically active lipophilic compound is at least partially dissolved in said blend.

10. The composition of claim 6, which contains not more than 1% by weight of water.

11. The composition of claim 6, wherein the micelle-forming lipid is monoacyl phosphatidyl choline (MAPC) or is pegalated monoacyl phosphatidyl ethanolamine.

12. The composition of claim 6, wherein said diacyl phospholipid is a bilayer-forming lipid.

13. The composition of claim 12, wherein the bilayer-forming lipid is phosphatidylcholine.

14. The composition of claim 6, wherein the micelle-forming lipid and the bilayer-forming lipid are in a mixture resulting from deacylation of a phospholipid.

15. The compositions of claim 14, wherein the phospholipid is lecithin.

16. The compositions of claim 15, wherein the phospholipid is partially enzyme-digested lecithin.

17. The composition of claim 16, wherein the enzyme-digested lecithin contains 20–80 mole % of monoacyl lipid fraction based on the total phospholipid content.

18. The composition of claim 16, wherein the enzyme-digested lecithin contains 60–80 mole % of monoacyl lipid fraction based on the total phospholipid content.

19. The composition of claim 16, wherein the biologically active compound is a hydrophobic neutral cyclic peptide.

20. The composition of claim 19 wherein the biologically active compound is a fungal metabolite.

21. The composition of claim 6, wherein the biologically active compound is a Cyclosporin.

22. The composition of claim 6, wherein the biologically active compound is Cyclosporin A.

23. The composition of claim 6, wherein the biologically active compound is astaxanthin.

24. The composition of claim 6, wherein the biologically active compound is a lipid soluble anti-infective or hormone compound, a cytototoxic compound, an anti-arrythmicc compound or a lipophilic peptide.

25. The composition of claim 6, comprising an excipient for modifying the physical characteristics of said composition.

26. The composition of claim 25, which is in the form of a hard wax.

27. The composition of claim 26, which is in the form of granules.

28. The composition of claim 26, which is spheronised.

29. The composition of claim 6, which is in the form of an extrudable soft solid or wax.

30. The composition of claim 25, which is in the form of a flowable powder.

31. The composition of claim 6, which is in the form of tablets.

32. The composition of claim 6, which is present within capsules.

33. The composition of claim 6, which contains a non-aqueous hydrophilic or lipophilic medium and is in the form of a liquid.

34. The composition of claim 33, wherein the liquid is present within capsules.

35. The composition of claim 6, which is in unit dosage form.

36. The composition of claim 6, for human oral administration.

37. A method for making an anhydrous or near anhydrous composition as defined in claim 6, which method comprises:

preparing a blend of at least one diacyl phospholipid and at least one monoacyl phospholipid which is derived from a partial enzyme digestion of diacyl phospholipids, said blend having a monoacyl phospholipid:diacyl phospholipid molar ratio of between 1:10 and 10:1, and said monoacyl phospholipid being a micelle-forming lipid, dissolving said blend as defined in claim 6 in an organic solvent to form a solution;

adding to the solution a lipophilic biologically active compound to be associated therewith;

removing the solvent and processing the resulting anhydrous or near anhydrous composition into an oral dosage form.

38. The method of claim 37, wherein the mixture of lipids further comprises a bilayer-forming lipid.

39. The method of claim 37, further comprising the step of formulating the resulting composition as a unit dosage form.

40. The method of claim 39, wherein the unit dosage form comprises a tablet.

41. The method of claim 39, wherein the unit dosage form comprises a capsule.

42. The method of claim 37, wherein the lipophilic pharmaceutical is a cyclic fungal metabolite.

43. The method of claim 42, wherein the lipophilic pharmaceutical is Cyclosporin A.

44. The method of claim 37, wherein the lipid mixture comprises a phospholipid and a lysolipid.

45. The composition of claim 6, wherein more than 60% of said lipid aggregates together with said associated biologically active lipophilic compound are capable of being passed through a 200 nm pore size filter.

46. The composition of claim 6, wherein at least 90% of said lipid aggregates together with said associated biologically active lipophilic compound are capable of being passed through a 200 nm pore size filter.

* * * * *